US006235486B1

(12) United States Patent
Young et al.

(10) Patent No.: US 6,235,486 B1
(45) Date of Patent: May 22, 2001

(54) METHOD FOR DETECTION OF BREAST CANCER

(75) Inventors: Charles Y. F. Young; Donald J. Tindall; George G. Klee, all of Rochester, MN (US)

(73) Assignee: Mayo Foundation for Medical Education & Research, Rochester, MN (US)

( * ) Notice: Subject to any disclaimer, the term of this patent is extended or adjusted under 35 U.S.C. 154(b) by 0 days.

(21) Appl. No.: 09/100,264

(22) Filed: Jun. 19, 1998

Related U.S. Application Data

(63) Continuation-in-part of application No. 60/050,963, filed on Jun. 20, 1997.

(51) Int. Cl.⁷ .................................................. G01N 33/53

(52) U.S. Cl. .................... 435/7.1; 435/7.21; 435/7.23; 435/330; 530/387.7; 530/388.1; 530/388.8

(58) Field of Search .................. 435/6, 7.21, 7.23, 435/7.1, 330, 344.1, 810; 424/138.1, 155.1, 156.1, 277.1, 573; 436/63, 64, 536, 813; 530/387.7, 388.8, 828, 388.1

(56) References Cited

U.S. PATENT DOCUMENTS

| | | | |
|---|---|---|---|
| 3,817,837 | 6/1974 | Rubenstein et al. | 195/103.5 R |
| 3,842,067 | 10/1974 | Sarantakis | 260/112.5 |
| 3,850,752 | 11/1974 | Schuurs et al. | 195/103.5 R |
| 3,862,925 | 1/1975 | Sarantakis et al. | 260/112.5 |
| 3,901,654 | 8/1975 | Gross | 23/230 B |
| 3,935,074 | 1/1976 | Rubenstein et al. | 195/103.5 R |
| 3,972,859 | 8/1976 | Fujino et al. | 260/112.5 LH |
| 3,984,533 | 10/1976 | Uzgiris | 424/12 |
| 3,996,345 | 12/1976 | Ullman et al. | 424/12 |
| 4,034,074 | 7/1977 | Miles | 424/1 |
| 4,092,408 | 5/1978 | Litt | 424/1 |
| 4,098,876 | 7/1978 | Piasio et al. | 424/1 |
| 4,105,602 | 8/1978 | Colescott et al. | 260/8 |
| 4,353,982 | 10/1982 | Gomez et al. | 435/7 |
| 4,371,515 | 2/1983 | Chu | 436/544 |
| 4,446,122 | 5/1984 | Chu et al. | 424/1.1 |
| 4,487,715 | 12/1984 | Nitecki et al. | 260/112.5 R |
| 4,629,783 | 12/1986 | Cosand | 530/324 |
| 4,757,048 | 7/1988 | Lewicki et al. | 514/11 |
| 4,792,528 | 12/1988 | Canfield et al. | 436/515 |
| 5,516,639 | 5/1996 | Tindall et al. | 435/7.4 |
| 5,614,372 | 3/1997 | Lilja et al. | 435/7.23 |
| 5,935,818 | 8/1999 | Israeli et al. | 435/69.3 |

FOREIGN PATENT DOCUMENTS

| | | | |
|---|---|---|---|
| 0 228 243 | 7/1987 | (EP) | G01N/33/577 |
| 0 297 913 | 1/1989 | (EP) | C12N/15/00 |
| 0 571 911 | 12/1993 | (EP) | C12Q/1/68 |
| 94/10343 | 5/1994 | (WO) | C12Q/1/68 |
| 94/27152 | 11/1994 | (WO) | G01N/33/574 |
| 95/03334 | 2/1995 | (WO) | C07K/16/40 |
| 95/28498 | 10/1995 | (WO) | C12Q/1/68 |
| 95/30758 | 11/1995 | (WO) | C12N/15/57 |
| 96/21042 | 7/1996 | (WO) | C12Q/1/68 |
| 96/26272 | 8/1996 | (WO) | C12N/15/12 |
| 96/26442 | 8/1996 | (WO) | C01N/33/574 |
| 96/34964 | 11/1996 | (WO) | C12N/15/57 |
| 97/01630 | 1/1997 | (WO) | C12N/9/64 |
| 97/07242 | 2/1997 | (WO) | C12Q/1/68 |
| 98/02748 | 1/1998 | (WO) | G01N/33/574 |

OTHER PUBLICATIONS

Yu et al. Induction of protsate specific antigen production by steroids and tamoxifen in breast cancer cell lines. Breast Cancer Research and Treatment. vol. 32 (1994) pp. 291–300.*

Allred, D.C., et al., "Association of p53 Protein Expression with Tumor Cell Proliferation Rate and Clinical Outcome in Node–negative Breast Cancer", *The Journal of the National Cancer Institute*, 85, 200–206 (1993).

Altman, P.L., et al., In: *Inbred and Genetically Defined Strains of Laboratory Animals: Part 1—Mouse and Rat*, Biology Handbooks, III, Federation of Animal Societies for Experimental Biology, Bethesda, MD, p. 21–29 (1979).

Andrews, P.E., et al., "Tumor–promoting Phorbol Ester Down–Regulates the Androgen Induction of Prostate–specific Antigen in a Human Prostate Adenocarcinoma Cell Line", *Cancer Research*, 52, 1525–1529 (Mar. 1992).

Angermann, A., et al., "Purification and Characterization of Human Salivary–Gland Prokallikrein from Recombinant Baculovirus–Infected Insect Cells", *Eur. J. Biochem.*, 206, 225–233 (1992).

Ashley, P.L., et al., "Kallikrein–Related mRNAs of the Rat Submaxillary Gland: Nucleotide Sequences of Four Distinct Types Including Tonin", *Biochemistry*, 24, 4512–4520 (1985).

Ashley, P.L., et al., "Tissue–Specific Expression of Kallikrein–Related Genes in the Rat", *Biochemistry*, 24, 4520–4527 (1985).

Baker, A., et al., "Human Kidney Kallikrein: cDNA Cloning and Sequence Analysis", *DNA*, 4, 445–450 (1985).

Berg, T., et al., "A Common Nomenclature for Members of the Tissue (Glandular) Kallikrein Gene Families", In: *Recent Progress on Kinins*, Fritz, H., et al., (eds.), Birkhauser Verlag, Basel, 19–25 (1992).

Bridon, D.P., et al., "Structural Comparison of Prostate–Specific Antigen and Human Glandular Kallikrein Using Molecular Modeling", *Urology*, 45, 801–806 (1995).

Carpino, L., et al., "The 9–Fluorenylmethoxycarbonyl Amino–Protecting Group", *Journal of Organic Chemistry*, 37, 3404–3409 (1972).

(List continued on next page.)

Primary Examiner—Jeffrey Stucker
Assistant Examiner—Ulrike Winkler
(74) Attorney, Agent, or Firm—Schwegman, Lundberg, Woessner & Kluth P.A.

(57) ABSTRACT

Breast cancer is detected by determining the presence of hK2 polypeptide or hK2 RNA in a physiological sample.

9 Claims, 11 Drawing Sheets

OTHER PUBLICATIONS

Chang, C., et al., "Solid Phase Peptide Synthesis Using Mild Base Cleavage of $N^\alpha$–Fluornylmethyloxycarbonylamino Acids, Exemplified by using a Synthesis of Dihydrosomatostatin", *Int. J. Peptide Protein Res.*, 11, 246–249 (1978).

Chapdelaine, P., et al., "High Level Expression in the Prostate of a Human Glandular Kallikrein mRNA Related to Prostate–Specific Antigen", *FEBS Letters*, 236, 205–208 (Aug. 1988).

Charlesworth, M.C., et al., "Detection of a Prostate–Specific Protein, Human Glandular Kallikrein (hK2), In Sera of Patients with Elevated Prostate–Specific Antigen Levels", *Urology*, 49, 487–493 (1997).

Christensson, A., et al., "Enzymatic Activity of Prostate–Specific Antigen and its Reactions with Extracellular Serine Proteinase Inhibitors", *Eur. J. Biochem.*, 194, 755–763 (1990).

Christensson, A., et al., "Serum Prostate Specific Antigen Complexed to α1–Antichymotrypsin as an Indicator of Prostate Cancer", *The Journal of Urology*, 150, 100–105 (1993).

Clements, J.A., "The Glandular Kallikrein Family of Enzymes: Tissue–Specific Expression and Hormonal Regulation", *Endocrine Reviews*, 10, 393–419 (1989).

Clements, J.A., "The Human Kallikrein Gene Family: A Diversity of Expression and Function", *Molecular and Cellular Endocrinology*, 99, C1–C6 (1994).

Clements, J.A., et al., "Glandular Kallikreins and Prostate–Specific Antigen Are Expressed in the Human Endometrium", *Journal of Clinical Endocrinology and Metabolism*, 78, 1536–1539 (1994).

Cohen, P., et al., "Biological Effects of PS as an IGFBP–3 Protease", *Program and Abstracts*, 74th Annual Meeting of the Endocrine Society, San Antonio, TX, Abstract No. 960 (Jun. 24–27, 1992).

Corey, E., et al., "Detection of Circulating Prostate Cells by Reverse Transcriptase–Polymerase Chain Reaction of Human Glandular Kallikrein (hK2) and Prostate–Specific Antigen (PSA) Messages", *Urology*, 50, 184–188 (Aug. 1997).

Deguchi, T., et al., "Detection of Micrometastatic Prostate Cancer Cells in Lymph Nodes by Reverse Transcriptase––Polymerase Chain Reaction", *Cancer Research*, 53, 5350–5354 (Nov. 15, 1993).

Deperthes, D., et al., "Isolation of Prostatic Kallikrein hK2, also Known as hGK–1, in Human Seminal Plasma", *Biochim. Biophys. Acta*, 1245, 311–316 (1995).

Digby, M., et al., "Human Prostate Specific Antigen (PSA) Gene: Structure and Linkage to the Kallikrein–like Gene", *Nucleic Acids Research*, 17, 2137 (1989).

Drinkwater, C.C., et al., "Kallikreins, Kinins and Growth Factor Biosynthesis", *Trends in Biochemical Science*, 13, 169–172 (1988).

Evans, B.A., et al., "Structure and Chromosomal Localization of the Human Renal Kallikrein Gene", *Biochemistry*, 27, 3124–3129 (1988).

Finlay, J.A., et al., "Development of a Dual Monoclonal Antibody Sandwich Assay for Human Glandular Kallikrein (hK2) with Minimal Cross Reactivity to Prostatic Specific Antigen (PSA)", *Clinical Chemistry*, 42, Abstracts, ASCC/CSCC 1996 Annual Meeting, Chicago, IL, Abstract No. 683, p. S259 (Jul. 28–Aug. 1, 1996).

Finlay, J.A., et al., "Development of a Dual Monoclonal Antibody Sandwich Assay for Human Glandular Kallikrein (hK2) with Minimal Cross Reactivity to Prostatic Specific Antigen (PSA)", *Conference Record*, 1996 International Symposium on Biology of Prostate Growth, Abstract No. 92, p. 79 (Mar. 28–31, 1996).

Finlay, J.A., et al., "Development of Monoclonal Antibodies (MAB) Specific for Human Glandular Kallikrein (hK2) and Their Utilization in Development of a Dual MAB Sandwich Assay for hK2 with Minimal Cross Reactivity to Prostate Specific Antigen (PSA)", *Conference Record*, XXIV Meeting of the International Society of Oncodevelopmental Biology and Medicine, Coronado, CA, 1 p. (Nov. 17–22, 1996).

Fugger, L., et al., "Expression of HLA–DR4 and Human CD4 Transgenes in Mice Determines the Variable Region β–chain T–cell Repertoire and Mediates an HLA–DR–Restricted Immune Response", *Proc. Natl. Acad. Sci. USA*, 91, 6151–6155 (Jun. 1994).

Fukushima, D., et al., "Nucleotide Sequence of Cloned cDNA for Human Pancreatic Kallikrein", *Biochemistry*, 24, 8037–8043 (1985).

Grauer, L.S., et al., "Identification of Human Glandular Kallikrein hK2 from LNCaP Cells", *Journal of Andrology*, 17, 353–359 (Jul./Aug. 1996).

Henttu, P., et al., "cDNA Coding for the Entire Human prostate Specific Antigen Shows High Homologies to the Human Tissue Kallikrein Genes", *Biochemical and Biophysical Research Communications*, 160, 903–910 (Apr. 28, 1989).

Henttu, P., et al., "Expression of the Gene Coding for Human Prostate–Specific Antigen and Related hGK–1 in Benign and Malignant Tumors of the Human Prostate", *Int. J. Cancer*, 45, 654–660 (1990).

Herrala, A., et al., "Human Prostate–Specific Glandular Kallikrein is Expressed as an Active and an Inactive Protein", *Clinical Chemistry*, 43, 279–284 (1997).

Hill, C.S., et al., "The Preparation of Monoclonal Antibodies which React Preferentially with Human Bone Alkaline Phosphatase and not Liver Alkaline Phosphatase", *Clinica Chemica Acta*, 186, 315–320 (1989).

Hsieh, M.L., et al., "Expression of Human Prostate–Specific Glandular Kallikrein Protein (hK2) in the Breast Cancer Cell Line T47–D", *Cancer Research*, 57, 2651–2656 (Jul. 1, 1997).

Husmann, D.A., et al., "Antipeptide Antibodies to Two Distinct Regions of the Androgen Receptor Localize the Receptor Protein to the Nuclei of Target Cells in the Rat and Human Prostrate", *Endocrinology*, 126, 2359–2360 (1990).

Jones, T.H., et al., "Bioregulatory Role of the Kallikrein––Kinin System in the Normal Pituitary Gland and Its Tumors", *Acta Endocrinologica*, 127, 481–484 (1992).

Killian, C.S., et al., "Mitogenic Response of Osteoblast Cells to Prostate–Specific Antigen Suggests and Activation of Latent TGF–β and a Proteolytic Modulation of Cell Adhesive Receptors", *Biochemical and Biophysical Research Communications*, 192, 940–947 (Apr. 30, 1993).

Klee, G.G., et al., "Immunochemiluminometric Assay for Measuring Human Glandular Kallikrein (hK2) in Human Serum", *Clinical Chemistry*, 43, Abstract No. 549, p. S225 (Jul. 24, 1997).

Kumar, A., et al., "Expression of Human Glandular Kallikrein, hK2, in Mammalian Cells", *Cancer Research*, 56, 5397–5402 (Dec. 1, 1996).

Kuus–Reichel, K., et al., "Production of IgG Monoclonal Antibodies to the Tumor Associated Antigen, CA–195", *Hybridoma*, 13, 31–36 (1994).

Laemmli, U.K., "Cleavage of Structural Proteins during the Assembly of the Head of Bacteriophage T4", *Nature*, 227, 680–685 (Aug. 15, 1970).

Le Beau, M.M., et al., "Report of the Committee on the Genetic Constitution of Chromosomes 18 and 19", *Cytogenet. Cell Genet.*, 51, 338–357 (1989).

Leinonen, J., et al., "Double–Labeled Time–Resolved Immunofluorometric Assay of Prostate–Specific Antigen and of its Complex with $\alpha_1$–Antichymotrypsin", *Clinical Chemistry*, 39, 2098–2103 (1993).

Liu, X.L., et al., "Identification of a Novel Serine Protease–like Gene, the Expression of Which is Down–Regulated during Breast Cancer Progression", *Cancer Research*, 56, 3371–3379 (Jul. 15, 1996).

Lottspeich, F., et al., "N–Terminal Amino Acid Sequence of Human Urinary Kallikrein Homology with Other Serine Proteases", *Hoppe–Seyler's Z. Physiol. Chem.*, 360, 1947–1950 (Dec. 1979).

Lövgren, J., et al., "Production of Recombinant PSA and HK2 and Analysis of Their Immunologic Cross–Reactivity", *Biochemical and Biophysical Research Communications*, 231, 888–895 (Aug. 24, 1995).

Lu, H.S., et al., "Human Urinary Kallikrein", *Int. J. Peptide Protein Res.*, 33, 237–249 (1989).

Luckow, V.A., et al., "Trends in the Development of Baculovirus Expression Vectors", *Bio/Technology*, 6, 47–55 (Jan. 1988).

Lundwall, Å., "Characterization of the Gene for Prostate–Specific Antigen, a Human Glandular Kallikrein", *Biochemical and Biophysical Research Communications*, 161, 1151–1159 (Jun. 30, 1989).

Lundwall, Å., et al., "Molecular Cloning of Human Prostate Specific Antigen cDNA", *FEBS Letters*, 214, 317–322 (Apr., 1987).

McCormack, R.T., et al., "Molecular Forms of Prostate–Specific Antigen and the Human Kallikrein Gene Family: A New Era", *Urology*, 45, 729–744 (May 1995).

Merrifield, R.B., "Solid Phase Peptide Synthesis—1. The Synthesis of a Tetrapeptide", *J. Am. Chem. Soc.*, 85, 2149–2154 (Jul. 1963).

Mikolajczyk, S.D., et al., "Ala217 is Important for the Catalytic Function and Autoactivation of Prostate–Specific Human Kallikrein 2", *Eur. J. Biochem.*, 246, 440–446 (1997).

Mikolajczyk, S.D., et al., "Human Glandular Kallikrein, hK2, Shows Arginine–Restriction Specificity and Forms Complexes with Plasma Protease Inhibitors", *The Prostate*, 34, 44–50 (Jan. 1998).

Mikolajczyk, S.D., et al., "Studies on the Substrate Specificity and Inhibition of Human Glandular Kallikrein (hK2)", Poster Abstract, Keystone Symposium, 1 p. (Mar. 28–31, 1996).

Montgomery, B., et al., "Hormonal Regulation of Prostate–Specific Antigen (PSA) Glycoprotein in the Human Prostatic Adenocarcinoma Cell Line, LNCaP", *The Prostate*, 21, 63–73 (1992).

Morris, B.J., "hGK–1: A Kallikrein Gene Expressed in Human Prostate", *Clinical and Experimental Pharmacology and Physiology*, 16, 345–351 (1989).

Murtha, P., et al., "Androgen Induction of a Human Prostate–Specific Kallikrein, hKLK2: Characterization of an Androgen Response Element in the 5' Promoter Region of the Gene", *Biochemistry*, 32, 6459–6464 (1993).

Nguyen, C., et al., "RT–PCR for hK2 mRNA: A New Assay For Detecting Circulating Prostate Cells", *Abstract*, 1997 Annual Meeting of the American Urological Association, New Orleans, 1 p. (1997).

Okaneya, T., et al., "Overexpression of a Prostate–Specific Glandular Kallikrein hK2 Protein Using a Baculovirus Expression System", *Conference Record*, Society for Basic Urologic Research, Spring Meeting, Abstract, 1 p. (May 13–14, 1994).

Paradis, G., et al., "Looking for Human Glandular Kallikrein–1 in the Prostate", *The Prostate*, 15, 343–353 (1989).

Piironen, T., et al., "Immunofluorometric Assay for Sensitive and Specific Measurement of Human Prostatic Glandular Kallikrein (hK2) in Serum", *Clinical Chemistry*, 42, 1034–1041 (1996).

Qiu, S.D., et al., "In Situ Hybridization of Prostate–Specific Antigen mRNA in Human Prostate", *The Journal of Urology*, 144, 1550–1556 (Dec. 1990).

Rahn, H.P., et al., "Expression of Human Salivary–Gland Kallikrein in Insect Cells by a Baculovirus Vector", In: *Recent Progress in Kinins*, Fritz, H., et al., (eds.), Birkhauser Verlag, Basel, 66–73 (1992).

Ransom, J.P., In: *Practical Competitive Binding Assay Methods*, C. V. Mosby Co., St. Louis, MO, 1–9, 54–61 (1976).

Riegman, P.H., et al., "Characterization of the Prostate–Specific Antigen Gene: A Novel Human Kallikrein–Like Gene", *Biochemical and Biophysical Research Communications*, 159, 95–102 (Feb. 28, 1989).

Riegman, P.H., et al., "Identification and Androgen–Regulated Expression of Two Major Human Glandular Kallikrein–1 (hGK–1) mRNA Species", *Molecular and Cellular Endocrinology*, 76, 181–190 (1991).

Riegman, P.H., et al., "The Prostate–Specific Antigen Gene and the Human Glandular Kallikrein–1 Gene are Tandemly Located on Chromosome 19", *FEBS Letters*, 247, 123–126 (Apr. 1989).

Ropers, H.H., et al., "Report of the Committee on the Genetic Constitution of Chromosome 19", *Cytogenet. Cell Genet.*, 55, 218–228 (1990).

Rosenberg, A.H., et al., "Vectors for Selective Expression of Cloned DNAs by T7 RNA Polymerase", *Gene*, 56, 125–135 (1987).

Saedi, M.S., et al., "Expression of the Serine Protease, Human Prostate Specific Glandular Kallikrein (hK2), in Mammalian Cells", *Conference Record*, ASBMB/ASIP/AAI Joint Meeting, Poster Abstract, 1 p. (Jun. 5, 1996).

Saedi, M.S., et al., "Overexpression of a Human Prostate–Specific Glandular Kallikrein, hK2, in *E. coli* and Generation of Antibodies", *Molecular and Cellular Endocrinology*, 109, 237–241 (Feb. 1995).

Sambrook, J., et al., In: *Molecular Cloning, a Laboratory Manual*, 2nd Edition, Cold Spring Harbor Laboratory Press, Cold Spring Harbor, NY, p. 12.2–12.15, (1989).

Schedlich, L.J., et al., "Kallikrein Genes: Cloning in Man and Expression in Rat Renal Hypertension", *Journal of Hypertension*, 6, S395–S398 (Dec. 1988).

Schedlich, L.J., et al., "Primary Structure of a Human Glandular Kallikrein Gene", *DNA*, 6, 429–437 (Nov. 5, 1987).

Schedlich, L.J., et al., "Three Alu Repeated Sequences Associated with a Human Glandular Kallikrein Gene", *Clinical and Experimental Pharmacology & Physiology,* 15, 339–344 (1988).

Schulz, P., et al., "Sequence of a cDNA Clone Encompassing the Complete Mature Human Prostate Specific Antigen (PSA) and an Unspliced Leader Sequence", *Nucleic Acids Research,* 16, 6226 (1988).

Scorer, C.A., et al., "Rapid Selection Using G418 of High Copy Number Transformants of *Pichia pastoris* for High–Level Foreign Gene Expression", *Bio/Technology,* 12, 181–184 (Feb. 1994).

Sutherland, G.R., et al., "Human Prostate–Specific Antigen (APS) is a Member of the Glandular Kallikrein Gene Family at 19q13", *Cytogenet. Cell Genet.,* 48, 205–207 (1988).

Takayama, T.K., et al., "Newer Applications of Serum Prostate–Specific Antigen in the Management of Prostate Cancer", *Seminars in Oncology,* 21, 542–553 (Oct. 1994).

Tijssen, P., In: *Practice and Theory of Enzyme Immunoassays,* Laboratory Techniques in Biochemistry and Molecular Biology, vol. 15, Burdon, R.H., (ed.), Elsevier, New York, 43–78, 95–121, 297–384 (1985).

Tindall, D.J., "hK2, A Novel Marker for Prostate Cancer", *Conference Record,* Sixth International Symposium on Biology and Clinical Usefulness of Tumor Markers, Barcelona, Spain, Abstract, 1 p. (Feb. 13–15, 1997).

van Leeuwen, B.H., et al., "Mouse Glandular Kallikrein Genes", *The Journal of Biological Chemistry,* 261, 5529–5535 (Apr. 25, 1986).

Vihinen, M., "Modeling of Prostate Specific Antigen and Human Glandular Kallikrein Structures", *Biochemical and Biophysical Research Communications,* 204, 1251–1256 (Nov. 15, 1994).

Wang, J., et al., "Purification and Characterization of Recombinant Tissue Kallikrein from *Escherichia coli* and Yeast", *Biochem. J.,* 276, 63–71 (1991).

Watt, K.W., et al., "Human Prostate–Specific Antigen: Structural and Functional Similarity with Serine Proteases", *Proc. Natl. Acad. Sci.,* USA, 83, 3166–3170 (May 1986).

Young, C.Y., et al., "Androgenic Regulation of Kallikrein Gene Expression in Human Prostate Cells", *Conference Record,* The Endocrine Society Annual Meeting, Abstract, 1 p. (1990).

Young, C.Y., et al., "Expression and Androgenic Regulation of Human Prostate–Specific Kallikreins", *Journal of Andrology,* 16, 97–99 (Mar./Apr. 1995).

Young, C.Y., et al., "Hormonal Regulation of Prostate–Specific Antigen Messenger RNA in Human Prostatic Adenocarcinoma Cell Line LNCaP", *Cancer Research,* 51, 3748–3752 (Jul. 15, 1991).

Young, C.Y., et al., "Prostate–Specific Human Kallikrein (hK2) as a Novel Marker for Prostate Cancer", *The Prostate Supplement,* 7, 17–24 (1996).

Young, C.Y., et al., "Tissue Specific and Hormonal Regulation of Human Prostate–Specific Glandular Kallikrein", *Biochemistry,* 31, 818–824 (1992).

* cited by examiner

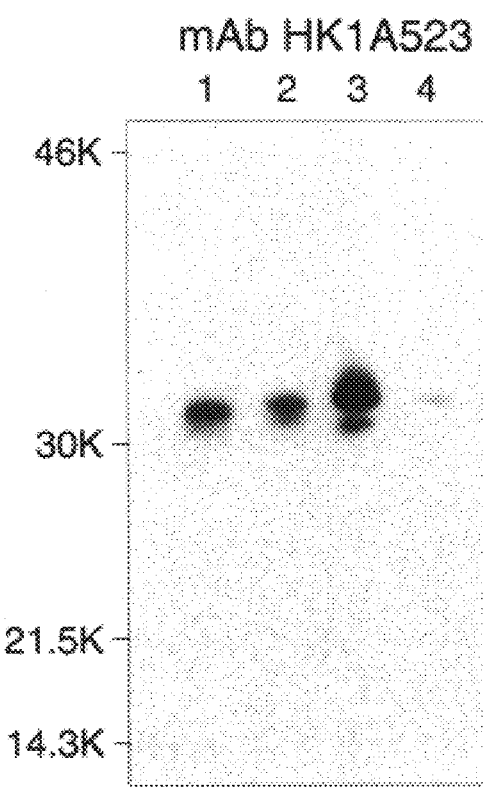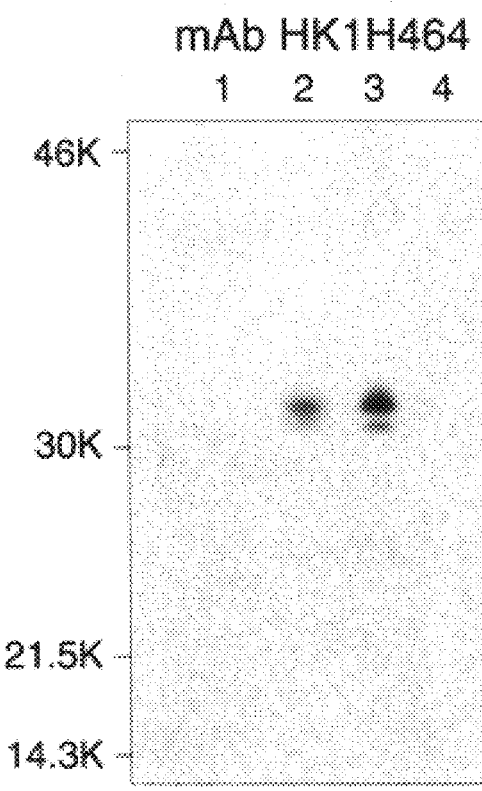

MW   PSA    hK2
    (710bp) (819bp)

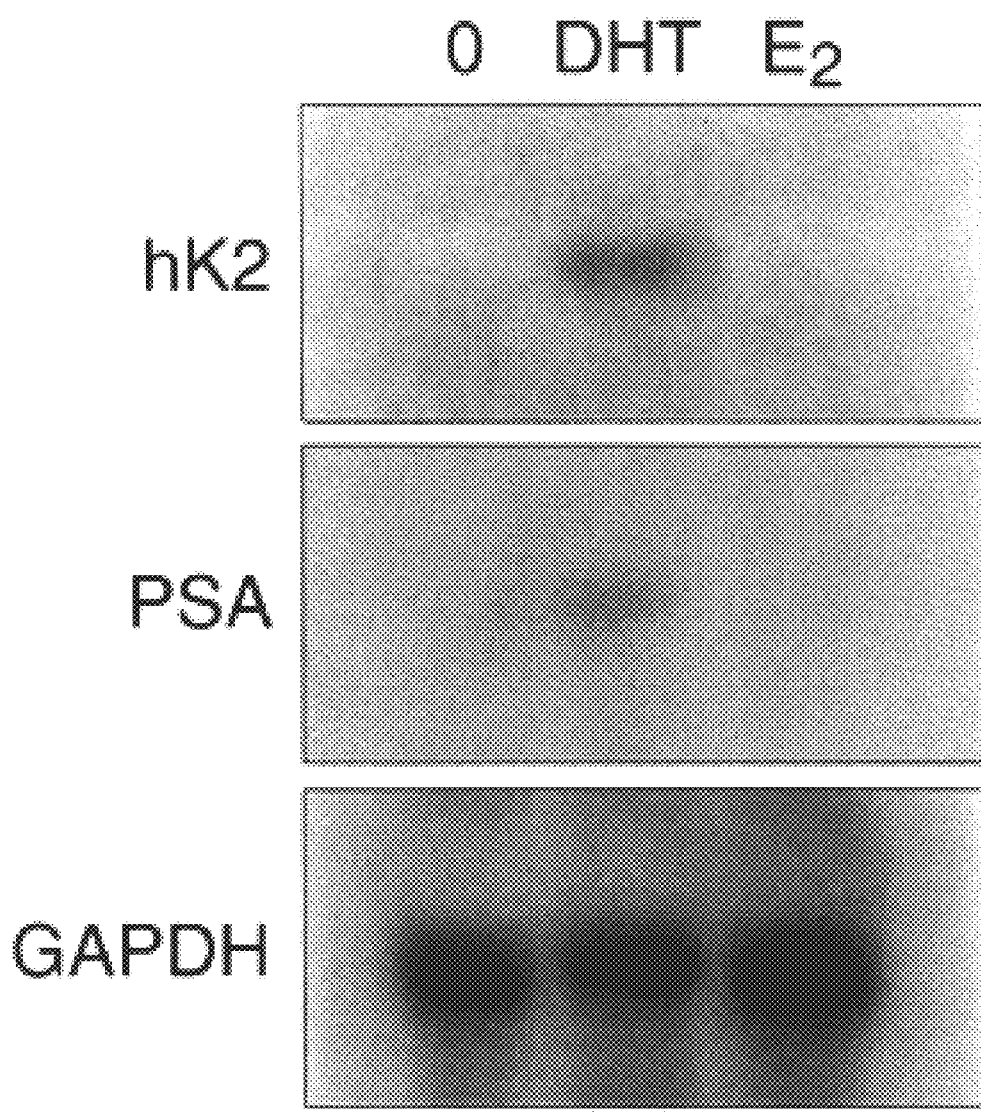

```
                                                            41
hK2:  IVGGWECEKHSQPWQVAV SHGWAHCGGVLVHPQWVLTAAHCLKKNSQVWLGRHN
hK3:  *****************L*A*R*R*V***************IRNK*VIL****S

56
      LFEPEDTGQRVPVSHSFPHPLYNMSLLKHQSLRPDEDSSHDLMLLRLSEPAKIT
      *"H***VFQH******DNRF*GD**************EL*

110                                              153
      DVVKVLGLPTQEPALGTTCYASGWGSIEPEEFLRPRSLQCVSLHLLSNDMCA
      *A***MD*********************TPKK****D*"VI***V**

162  167
      RAYSEKVTEFMLCAGLWTGGKDTCGGDSGGPLVCNGVLQGITSWGPEPCALPEKP
      QVHPQ*K*R*SS****************S****R*

217           237
      AVYTKVVHYRKWIKDTIAANP
      SL**************V***
```

FIG. 8

FIG. 9 hK2 cDNA

```
       pphK2                                                                                    phK2
-76  CAGCATGTGGGACCTGGTTCTCTCCATGCCCTGTCTGTGGGGTGCACTGGTGCCGTGCCCCTCATCCAGTCTCGGA
     1▶MetTrpAspLeuValLeuSerIleAlaLeuSerValGlyCysThrGlyAlaValProLeuIleGlnSerArg                                                                 1▶
                                                                                                hK
                                                                                                1▶
2    TTGTGGGAGGGTGCTGTGAGAAGCATTCCCAACCCTGTGTGGCTGTGTACAGTCATGATGGCACACTGT
     IleValGlyGlyTyrGlyCysGluLysHisSerGlnProTrpGlnValAlaValTyrSerHisGlyTrpAlaHisCys
79   GGGGGTGTCCTGGTGCACCCCCAGTGGGTGCTCACAGCTGCCATTGCCTAAAGAAGACCTAAAGAAGAATAGCCAGGTCTGGCTGGG
27▶  GlyGlyValLeuValHisProGlnTrpValLeuThrAlaAlaHisCysLeuLysLysAsnSerGlnValTrpLeuGl
156  TCGGCACAACCTGTTTGAGCCTGAAGACACAGCCAGGTCCCTGTCAGCCACACCTTCCACACCCGCTCTACA
52▶  yArgHisAsnLeuPheGluProGluAspThrGlnArgValProValSerHisSerPheProHisProLeuTyrA
233  ATATGAGCCTTCTGAAGCATCAAAGCTTAGACCAGATGAAGACTCCAGCCATGACCTCATGCTCCTGCGCCTGTCA
78▶  snMetSerLeuLeuLysHisSerLeuArgProAspSerLeuArgProAspAspLeuMetLeuLeuArgLeuSer
310  GAGCCTGCCAAGATCACAGATGTGTGAAGGTTCCTGGGCTGCCCAGGAGCCAGACTGGGGACCACCTGCTA
104▶ GluProAlaLysIleLlyIleThrAspValLysGlyProGluGlyProThrGlnArgValProProThrCysTy
387  CGCCTCAGGCTGGGGCAGCATCGAACCAGAGAGTTCTTGCGCCCCAGAGTCTTCAGTGTGTGAGCCTCCATCTCC
129▶ rAlaSerGlyTrpGlySerIleGluProGluGluPheLeuArgProArgSerLeuGlnCysValSerLeuHisLeuL
464  TGTCCAATGACATGTGTGCTTACTCTGAGAAGGTGACAGAGTTCATGTGTGTGGCTCTGGACAGGT
155▶ euSerAsnAspMetCysAlaArgAlaTyrSerGluLysValThrGluPheMetLeuCysAlaGlyLeuTrpThrGly
541  GGTAAAGACACTTGTGGGGGTGATTCTGGGGGTCCACTTGTCTGTAATGGTGTGCTTCAAGGTATCACATCATGGGG
181▶ GlyLysAspThrCysGlyGlyAspSerGlyGlyProLeuValCysAsnGlyValLeuGlnGlyIleThrSerTrpG
618  CCCTGAGCCATGCCTGCCCTGAAAAGCCTGTGTACACCAAGGTGGTGCATTACCGGAAGTGGATCAAGGAC
206▶ lyProGluProCysAlaLeuProGluLysProAlaValTyrThrLysValValHisTyrArgLysTrpIleLysAsp
694  ACCATCGCAGCCAACCCCTGAGTGCCCT
232▶ ThrIleAlaAlaAsnPro···ValPro
```

METHOD FOR DETECTION OF BREAST CANCER

CROSS-REFERENCE TO RELATED APPLICATION

This application is a continuation-in-part of U.S. provisional application Ser. No.60/050,963, filed Jun. 20, 1997, which is incorporated by reference herein.

STATEMENT OF GOVERNMENT RIGHTS

This invention was made with the support of the U.S. Government via grants from the National Institutes of Health (Grant Nos. CA70892 and DK41995). The Government may have certain rights in this invention.

BACKGROUND OF THE INVENTION

Breast cancer is a leading cause of mortality and morbidity among women. One of the priorities in breast cancer research is the discovery of new biochemical markers which can be used for diagnosis, prognosis and monitoring of breast cancer. The prognostic usefulness of these markers depends on the ability of the marker to distinguish between patients with breast cancer who require aggressive therapeutic treatment and patients who should be monitored. Because breast cancer is one of a few cancers that is dependent on steroid hormones and their receptors, analysis of estrogen receptor (ER) and progesterone receptor (PR) status is currently routinely performed as an aid in prognosis and selection of therapy. Other markers or indicators which are currently employed to diagnose and monitor breast cancer include: tumor size, age, aneuploidy, mitotic activity and Ki67 (Allred et al., *J. Natl. Cancer Inst.*, 85, 200–206 (1993)).

Mutation of the p53 tumor suppressor gene is one of the most commonly known genetic defects in human cancer, including breast cancer. Mutations in p53 result in the expression of a mutant protein which can accumulate to high concentrations. Overexpression of p53 protein is an independent predictor of early disease recurrence (Allred et al., supra). The accumulation of p53 protein has also been found to be an independent marker of shortened survival (Thor et al., *J. Nat'l Cancer Inst.*, 84, 845–855 (1992)). However, the majority of tumors that are estrogen and/or progesterone receptor-positive do not express mutant p53 protein.

Prostate cancer, like breast cancer, is dependent on steroid hormones. One of the hallmarks of prostate cancer is the appearance in serum, at elevated concentrations, of a 30–33 kD glycoprotein, prostate-specific antigen (PSA) (Oesterling, *J. Urol.*, 145, 907–923 (1991)). PSA is a kallikrein-like serine protease that was thought to be exclusively produced by epithelial cells lining the acini and ducts of the prostate gland (Papsidero et al., *J. Natl. Cancer Inst.*, 66, 37–41 (1981); Lilja, *J. Clin. Invest.*, 76, 1899–1903 (1985); Watt et al., *Proc. Natl. Acad. Sci. USA*, 83, 3166–3170 (1986)). Because of its tissue specificity, PSA has been widely used as a marker to diagnose and monitor prostate cancer (Stamey et al., *N. Engl. J. Med.*, 317, 909–916 (1987); Catalona et al., *N. Engl. J. Med.*, 324, 1156–1161 (1991)).

However, a number of studies have demonstrated the presence of PSA in non-prostate tissue. For example, Yu et al. (*Breast Cancer Res. Treat.*, 32, 291–300 (1994)) reported that the steroid hormone receptor-positive breast carcinoma cell lines T47-D and MCF-7 can be stimulated by androgens, progestins, antiestrogens, mineralocorticoids and glucocorticoids to produce PSA. Diamandis et al. (*Breast Cancer Res. Treat.*, 32, 301–310 (1994)) reported that 30% of female breast tumor cytosolic extracts contain PSA immunoreactivity. In addition, it is disclosed in Diamandis (WO 94/27152) that the presence of PSA in breast tumors is associated with tumors that express ER and/or PR. Thus, it has been speculated that PSA may be useful as a prognostic marker for breast cancer (Yu et al., *Cancer Res.*, 55, 2104–2110 (1995); Diamandis (WO 94/27152)).

Nevertheless, it is unclear whether PSA is correlated with ER and/or PR receptor status or has prognostic significance. In an analysis of a subset of breast tumors for PR and ER status, Yu et al. (*Clin. Biochem.*, 27, 75 (1994)) disclose that immunoreactive PSA was only associated with PR, and no relationship was found between immunoreactive PSA and ER. In contrast, a 1995 report by Yu et al. (*Cancer Res.*, 55, 2104 (1995)) found that PSA and ER were independent, although collaborative, markers for the prognosis of breast cancer. The authors also report that the presence or absence of PSA had no additional prognostic significance in steroid receptor-positive patients.

There is, therefore, a need for an inexpensive and simple prognostic and/or diagnostic marker for breast cancer that can function independently of, or in combination with, current employed markers.

SUMMARY OF THE INVENTION

The invention provides methods to determine the amount or presence of hK2 RNA or polypeptide in mammalian breast cells, e.g., breast tissue samples, or cells obtained from physiological fluids or tissue samples, e.g., blood or lymph node, which may comprise metastatic breast cancer cells. As described hereinbelow, hK2 is produced at a higher level relative to PSA by a breast cancer cell line, T47-D, after androgen stimulation. Moreover, T47-D cells produce significantly more hK2 than PSA (2–3 fold) when these cells are induced with mineralocorticoids, glucocorticoids or progestins. In contrast, estrogens failed to induce hK2. Therefore, the determination of the presence or amount of hK2 RNA or polypeptide may be useful in the diagnosis, treatment and/or monitoring of the progression or remission of breast cancer.

The invention thus provides a method for detecting hK2 nucleic acid in breast cells. The method comprises subjecting an amount of RNA obtained from a sample comprising breast cells to an amplification reaction so as to yield an amount of amplified nucleic acid, i.e., RNA or DNA. The amplified nucleic acid is then detected or determined. Methods to amplify nucleic acid molecules are well known to the art including, but not limited to, self-sustained sequence-specific replication (3SR) (Gebinoga et al., *Eur. J. Biochem.*, 235, 256 (1996); Fahy et al., *PCR Methods Appl*, 1, 25 (1991); Guatelli et al., *Proc. Nat'l Acad. Sci. U.S.A.*, 87, 1874 (1990)), nucleic acid sequence-based amplification (NASBA) (Compton, *Nature*, 350, 91 (1991)), strand displacement amplification (SDA) (Walker et al., *Proc. Nat'l Acad. Sci. U.S.A.*, 89, 392 (1992); Walker et al., *Nucl. Acid Res.*, 20, 1691 (1992)), probe cyclization (Landgren, *Trends in Gen.*, 2, 199 (1993)), or a Q beta replicase, Sp6, T7, or T3 RNA polymerase based amplification system. See, for example, U.S. Pat. Nos. 5,622,820, 5,629,153, 5,532,126, 5,573,914 and 5,514,545.

The invention also provides a method to detect hK2 cDNA. The method comprises contacting an amount of DNA obtained by reverse transcription (RT) of RNA from a sample comprising breast cells with a plurality of oligonucleotide primers, preferably at least two oligonucleotide primers, at least one of which is an hK2-specific oligonucleotide, in an amplification reaction so as to yield an amount of amplified hK2 DNA. A preferred amplification reaction is a polymerase chain reaction (PCR). The presence of the amplified hK2 DNA is then detected. Preferably, the source of the sample to be tested is human tissue, more preferably, a human breast tissue biopsy sample, obtained from a male or female.

The invention further provides a method for detecting breast cancer in a human. The method comprises contacting an amount of DNA obtained by RT of RNA from a human physiological sample which comprises cells suspected of containing hK2 RNA, with an amount of at least two oligonucleotides under conditions effective to amplify the DNA by a polymerase chain reaction, so as to yield an amount of amplified hK2 DNA. At least one oligonucleotide is an hK2-specific oligonucleotide. The presence or amount of the amplified hK2 DNA is detected or determined, and the presence or amount of the amplified hK2 DNA is then correlated to the presence or absence of breast cancer in said human.

Also provided is a diagnostic method for detecting hK2 RNA. The method comprises extracting RNA from a physiological sample obtained from a human. The extracted RNA is reverse transcribed to yield DNA. The DNA is contacted with an amount of at least two oligonucleotides effective to amplify the DNA to yield an amount amplified hK2 DNA, wherein at least one oligonucleotide is an hK2-specific oligonucleotide. The presence or amount of the amplified hK2 DNA is then detected or determined. The presence or amount of the amplified hK2 DNA is correlated to the presence or absence of breast cancer in said human.

A preferred method of the invention combines RT-PCR detection of hK2 transcripts with detection of other gene products associated with breast cancer, e.g., ER, PR, p53 or PSA. Combined detection of two or more gene products may provide greater diagnostic certainty or yield more informative staging or prognostic information. Combined detection may also be helpful in differentiating breast cancers that are responsive to hormonal therapy from those which are not.

The presence or amount of hK2 RNA, or hK2 polypeptide, that changes over time, e.g., in breast tissue, may be reasonably expected to indicate the progression ore remission of breast cancer, as well as the presence of previously undiagnosed metastatic disease, when hK2 RNA or polypeptide is found in bodily fluids and/or in non-breast tissue in females or in non-breast and non-prostate tissue in males. Early detection of metastatic disease provides a "lead time" during which alternative therapeutic strategies, including those that may not exist at the time of surgery but are subsequently developed, can be evaluated. Moreover, because hK2 expression is androgen-dependent, hK2 RNA levels in breast tissue, peripheral blood or other bodily tissue or fluid may be used as a marker during hormone therapy. hK2 levels are preferably monitored periodically during the course of hormone therapy. It may be advantageous to also determine hK2 levels before commencement of therapy, and periodically after the conclusion of a therapeutic regimen.

Thus, the present invention provides a method for monitoring the course, progression or remission of breast cancer. This method comprises contacting an amount of DNA obtained by reverse transcription of RNA from a physiological sample obtained from a human afflicted with breast cancer with an amount of at least two oligonucleotides, at least one of which an hK2-specific oligonucleotide, effective to amplify the DNA to yield an amount of amplified hK2 DNA. The presence or amount of the amplified hK2 DNA is detected or determined. At least one point later in time, another sample is taken and the amount of amplified hK2 DNA detected or determined. Then the amounts of amplified hK2 DNA, obtained at least at two different time points, are compared.

The invention also provides a diagnostic kit for detecting hK2 nucleic acid, e.g., RNA, in a physiological sample suspected of containing hK2 nucleic acid. The kit comprises packaging containing, separately packaged, a) an amount of a first hK2-specific oligonucleotide, wherein the oligonucleotide consists of at least about 7–50 nucleotides, and wherein the oligonucleotide has at least about 80% identity to SEQ ID NO:8, and (b) an amount of a second hK2-specific oligonucleotide, wherein the oligonucleotide consists of at least about 7–50 nucleotides, and wherein the oligonucleotide has at least about 80% identity to a sequence that is complementary to SEQ ID NO:8. Preferably, the second hK2-specific oligonucleotide comprises SEQ ID NO:11.

The invention further provides immunological methods for detecting or determining the presence or progression of breast cancer. The method comprises contacting an amount of an agent, which binds to hK2 and which does not bind to hK3, with a sample comprising mammalian cells, e.g., breast cells, so as to form a binary complex comprising the agent and the cells. The presence or amount of complex formation in the sample is then detected or determined. The presence or amount of the complex provides an indication of the presence or absence of breast cancer. A preferred agent for use in the method is an antibody. The term "antibody" includes human and animal monoclonal antibodies (mAbs), and preparations of polyclonal antibodies, as well as antibody fragments, synthetic antibodies, including recombinant antibodies, chimeric antibodies, including humanized antibodies, anti-idiotypic antibodies and derivatives thereof. To prepare antibodies which bind to hK2 and not to hK3, isolated hK2 polypeptides including the prepro, pro or mature forms of hK2 polypeptide, isolated hK2 peptides, as well as variants and subunits thereof, can be used to prepare populations of antibodies. These antibodies in turn can be used as the basis for direct or competitive assays to detect and quantify hK2 polypeptides (or "protein") in samples derived from tissues such as breast tissue, bone marrow and lymph nodes, and physiological fluids which comprise cells.

Thus, the invention provides a method for diagnosis, prognosis or treatment of breast cancer. The method comprises conducting a biological assay on a sample of breast tumor tissue to detect the presence of hK2 in said sample. The assay is capable of detecting a concentration of hK2 of at least as low as about 0.001 to about 0.5, preferably about 0.01 to about 0.1, more preferably about 0.02 to about 0.05, ng of hK2 per mg of total protein of said tumor tissue. Upon detecting hK2 in said sample, the human is classified as to their hK2 status for the purpose of diagnosis, prognosis or treatment of breast cancer.

Further provided is a method for monitoring the progression of breast cancer, for example, during hormone therapy. The method comprises contacting an amount of an agent which binds to hK2 and which does not bind to hK3, with the cells of a human tissue sample so as to form a binary complex comprising the agent and the cells. The presence or amount of complex formation in the sample is detected or determined. A subsequent sample is contacted with a second amount of the agent so as to form a second binary complex. The presence or amount of the second binary complex is compared to the presence or amount of the first binary complex. A change in the amount of complex formation is indicative of the progression of breast cancer in said human.

The invention also provides a diagnostic kit for determining hK2 polypeptide in cells of a mammalian breast tissue sample. The kit comprises packaging, containing, separately packaged, a) a known amount of a first agent which specifically binds to hK2 and not to hK3, b) a known amount of a second agent which does not bind to hK2 and which binds to the first agent, wherein the second agent is detectably labeled or binds to a detectable label, and c) instructions means, such as a printed package insert, label, audio or video tape, instructing the use of a) and b) to carry out the methods described hereinabove.

The invention also provides a non-amplification based method to detect hK2 in breast cells. The method includes contacting a sample of RNA obtained from mammalian breast cells with an amount of a probe comprising at least a portion of the hK2 gene so as to form a binary complex. Then the amount or presence of the binary complexes formed is detected or determined. The contacting step may occur in solution or in solid phase, e.g., on a nitrocellulose or nylon membrane, having the RNA sample.

The invention further provides a method to detect breast cancer in a mammal. This method comprises contacting a first amount of a labeled probe comprising a preselected DNA comprising at least a portion of the hK2 gene with a sample which comprises mammalian breast cells that are suspected of containing hK2 RNA (the test sample) for a sufficient time to form binary complexes between at least a portion of an amount of probe and the cells in the sample. Then the amount of binary complexes is detected or determined relative to the amount of binary complexes formed between a second amount of the probe and a control sample comprising mammalian cells which do not express hK2 RNA. A relative greater amount of binary complexes formed in the test sample is indicative of breast cancer.

Also provided is a method to detect a mammal at risk or, or having, breast cancer. The method comprises contacting an amount of a labeled probe comprising a preselected DNA comprising the hK2 gene, or a portion thereof, with RNA isolated from a mammalian breast sample for a sufficient time to form binary complexes between at least a portion of the probe and the RNA. The absence or presence of the binary complexes formed is compared to the absence or presence of control binary complexes formed between a portion of a second amount of the probe and RNA obtained from a sample comprising mammalian cells which do not express hK2 RNA. Complexes formed with the test sample which are different than complexes formed with the control sample are indicative of a mammal at risk of, or having, breast cancer.

Further provided is a method for detecting hK2-specific RNA in a mammalian physiological sample which comprises cells. The method includes subjecting RNA that is isolated from the sample which is suspected of containing hK2 RNA to an amplification reaction under reaction conditions sufficient to amplify at least a portion of the hK2-specific RNA to produce an amplification product. Then it is determined whether the amplification product is different than an amplification product obtained by subjecting RNA isolated from a control sample which does contain hK2-specific RNA to an amplification reaction under reaction conditions sufficient to amplify at least a portion of hK2-specific RNA.

Also provided is a method for detecting hK2-specific RNA in a physiological sample obtained from a mammal. The method comprises contacting an amount of a labeled probe comprising a preselected DNA comprising the hK2 gene, or a portion thereof, with RNA isolated from mammalian breast cells for a sufficient time to form binary complexes between at least a portion of the probe and the RNA. Then the presence or absence of the binary complexes formed is detected or determined relative to the absence or presence of control binary complexes formed between a second amount of said probe and RNA obtained from a sample comprising mammalian cells which do not express hK2 RNA.

BRIEF DESCRIPTION OF THE FIGURES

FIG. 8. A comparison of the amino acid sequence of the mature form of hK2 (SEQ ID NO:1) and the mature form of PSA (SEQ ID NO:3). Underlining indicates regions of hK2 and PSA sequences which are nonhomologous.

FIG. 9. The nucleotide sequence, and corresponding amino acid sequence, of prepro hK2 (SEQ ID NO:8 and SEQ ID NO:7, respectively) and pro hK2 (SEQ ID NO:6 and SEQ ID NO:5, respectively).

DETAILED DESCRIPTION OF THE INVENTION

Definitions

Figure 1:
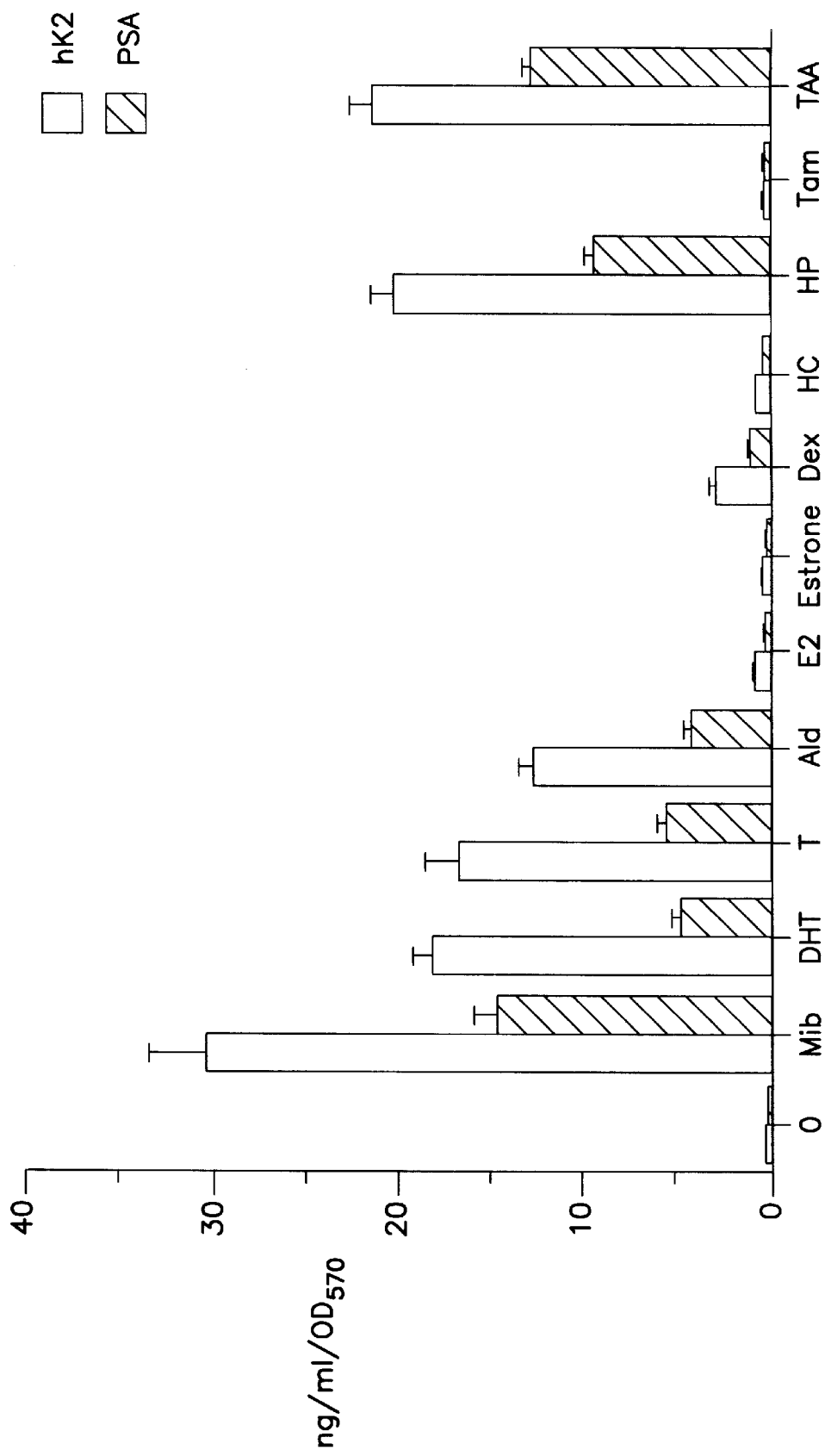
FIG. 1. Production of PSA and hK2 by T47-D cells after stimulation by various steroids. T47-D cells which had been cultured in serum-free RPMI 1640 media were treated with various steroids for 4 days. The spent media were harvested for hK2 and PSA quantitative analysis by immunoassay. Mib: mibolerone, 3.2 nM; DHT: dihydrotestosterone, 200 nM; T: testosterone, 200 nM; Ald: aldosterone, E2:estradiol, 1 $\mu$M; estrone: 1 $\mu$M; Dex: dexamethasone, 1 $\mu$M; HC: hydrocortisone, 1 $\mu$M; HP: 11-$\beta$-hydroxyprogesterone, 1 $\mu$M; Tam: tamoxifen, 1 $\mu$M; TAA: triamcinolone acetonide, 1 $\mu$M.

As used herein, "amplified" hK2 DNA or RNA is defined to mean hK2 DNA or RNA in a sample, which was subjected to an amplification reaction, and that is present in an amount that is greater than, e.g., 10, preferably $10^4$, and more preferably greater than $10^6$, times, the amount of hK2 DNA or RNA which was present in the sample prior to amplification.

As used herein, the term "hK2-specific oligonucleotide" or "hK2-specific primer" means a nucleic acid, e.g., DNA, sequence that has at least about 80%, more preferably at least about 90%, and more preferably at least about 95%, contiguous sequence identity or homology to SEQ ID NO:2 (the DNA sequence encoding the mature form of hK2) or its complementary sequence, preferably in regions of SEQ ID NO:2 that are divergent from nucleotide sequences encoding the mature form of PSA (SEQ ID NO:4; the DNA sequence encoding the mature form of PSA). An oligonucleotide or primer of the invention has at least about 7–50, preferably at least about 10–40, and more preferably at least about 15–35, nucleotides. Preferably, the oligonucleotide primers of the invention comprise at least about 7 nucleotides at the 3' of the oligonucleotide primer which have at least about 80%, more preferably at least about 85%, and more preferably at least about 90%, contiguous identity to SEQ ID NO:2, SEQ ID NO:6 (DNA encoding pro hK2), or SEQ ID NO:8 (DNA encoding prepro hK2), or sequences complementary thereto. The oligonucleotides of the invention may also include sequences which are unrelated to hK2 nucleic acid sequences, e.g., they may encode restriction endonuclease recognition sequences. A preferred hK2-specific oligonucleotide of the invention comprises SEQ ID NO:9. Another preferred hK2-specific oligonucleotide of the invention comprises SEQ ID NO:10. Yet another preferred hK2-specific oligonucleotide of the invention comprises SEQ ID NO:11.

As used herein, the term "hK2 polypeptide" includes the prepro, pro and mature forms of hK2 polypeptides, as well as variants and/or subunits of those polypeptides. Thus, for example, a mature hK2 polypeptide having the amino acid sequence shown in FIG. 8 (SEQ ID NO:1), as well as variant hK2 polypeptides which share at least 90% homology with SEQ ID NO:1 in regions which are not identified by underlining in FIG. 8, are within the scope of the term "hK2 polypeptide." Preferably, the hK2 polypeptides, variant polypeptides, or subunits thereof, are biologically active.

The biological activity of an hK2 polypeptide of the invention can be detected by methods well known to the art including, but not limited to, the ability to react with antibodies specific for hK2 polypeptides. Thus, the hK2 polypeptides of the invention possess antigenic function in common with the mature hK2 molecule of FIG. 8, in that said polypeptides are also definable by antibodies which bind specifically thereto, but which do not cross-react with PSA (or hK1). Preferably, said antibodies react with antigenic sites or epitopes that are also present on the mature hK2 molecule of FIG. 8. Antibodies useful to define common antigenic function are described in detail in U.S. Pat. No. 5,516,639, e.g., polyclonal antisera prepared in vivo against hK2 subunit 41–56, and U.S. application Ser. No. 08/622,046, the disclosures of which are incorporated by reference herein.

Moreover, a variant hK2 polypeptide or subunit thereof, or a subunit of an hK2 polypeptide, has at least about 10%, preferably at least about 50%, and more preferably at least about 90%, the biological activity of an hK2 polypeptide comprising the amino acid sequence of SEQ ID NO:1 (mature hK2), SEQ ID NO:5 (pro hK2) or SEQ ID NO:7 (prepro hK2). Preferably, the variant hK2 polypeptides of the invention have at least one amino acid substitution relative to the corresponding wild type hK2 polypeptide. A preferred variant hK2 polypeptide comprises SEQ ID NO:12, i.e., a mature hK2 polypeptide having an alanine to valine substitution at amino acid position 217.

"Isolated hK2 nucleic acid" is RNA or DNA containing greater than 7, preferably 15, and more preferably 20 or more, sequential nucleotide bases that are complementary to the non-coding or coding strand of the native hK2 RNA or DNA, or hybridizes to said RNA or DNA and remains stably bound under stringent conditions. Preferably, the isolated nucleic acid encodes a biologically active hK2 polypeptide, a variant thereof, or a subunit thereof.

Thus, the RNA or DNA is isolated in that it is free from at least one contaminating nucleic acid with which it is normally associated in the natural source of the nucleic acid and is preferably substantially free of any other mammalian RNA or DNA. The phrase "free from at least one contaminating nucleic acid with which it is normally associated" includes the case where the nucleic acid is reintroduced into the source or cell from which it was derived but is in a different chromosomal location or is otherwise flanked by nucleic acid sequences not normally found in the source or cell. An example of isolated hK2 nucleic acid is RNA or DNA that encodes a biologically active hK2 polypeptide sharing at least 90% sequence identity with the PSA-homologous regions of the hK2 peptide of FIG. 8, as described above. The term "isolated, purified" as used with respect to an hK2 polypeptide is defined in terms of methodologies well known to the art, e.g., see U.S. application Ser. No. 08/622,046.

As used herein, the term "recombinant nucleic acid," i.e., "recombinant DNA" refers to a nucleic acid, i.e., to DNA that has been derived or isolated from any appropriate tissue source, that may be subsequently chemically altered in vitro, and later introduced into target host cells, such as cells derived from animal, plant, insect, yeast, fungal or bacterial sources. An example of recombinant DNA "derived" from a source, would be a DNA sequence that is identified as a useful fragment encoding hK2, or a -fragment or variant thereof, and which is then chemically synthesized in essentially pure form. An example of such DNA "isolated" from a source would be a useful DNA sequence that is excised or removed from said source by chemical means, e.g, by the use of restriction endonucleases, so that it can be further manipulated, e.g., amplified, for use in the invention, by the methodology of genetic engineering.

Therefore, "recombinant DNA" includes completely synthetic DNA sequences, semi-synthetic DNA sequences, DNA sequences isolated from biological sources, and DNA sequences derived from introduced RNA, as well as mixtures thereof. Generally, the recombinant DNA sequence is not originally resident in the genome of the host target cell which is the recipient of the DNA, or it is resident in the genome but is not expressed, or not highly expressed.

As used herein, "chimeric" means that a vector comprises DNA from at least two different species, or comprises DNA from the same species, which is linked or associated in a manner which does not occur in the "native" or wild type of the species.

"Control sequences" is defined to mean DNA sequences necessary for the expression of an operably linked coding sequence in a particular host organism. The control sequences that are suitable for prokaryotic cells, for example, include a promoter, and optionally an operator sequence, and a ribosome binding site. Eukaryotic cells are known to utilize promoters, polyadenylation signals, and enhancers.

"Operably linked" is defined to mean that the nucleic acids are placed in a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contiguous and in reading phase. However, enhancers do not have to be contiguous. Linking is accomplished by ligation at convenient restriction sites. If such sites do not exist, synthetic oligonucleotide adaptors or linkers are used in accord with conventional practice.

"Southern analysis" or "Southern blotting" is a method by which the presence of DNA sequences in a restriction endonuclease digest of DNA or DNA-containing composition is confirmed by hybridization to a known, labeled oligonucleotide or DNA fragment. Southern analysis typically involves electrophoretic separation of DNA digests on agarose gels, denaturation of the DNA after electrophoretic separation, and transfer of the DNA to nitrocellulose, nylon, or another suitable membrane support for analysis with a radiolabeled, biotinylated, or enzyme-labeled probe as described in sections 9.37–9.52 of Sambrook et al., supra.

"Northern analysis" or "Northern blotting" is a method used to identify RNA sequences that hybridize to a known probe such as an oligonucleotide, DNA fragment, cDNA or fragment thereof, or RNA fragment. The probe is labeled with a radioisotope such as $^{32}p$, by biotinylation or with an enzyme. The RNA to be analyzed can be usually electrophoretically separated on an agarose or polyacrylamide gel, transferred to nitrocellulose, nylon, or other suitable membrane, and hybridized with the probe, using standard techniques well known in the art such as those described in sections 7.39–7.52 of Sambrook et al., supra.

"Stringent conditions" are those that (1) employ low ionic strength and high temperature for washing, for example, 0.015 M NaCl/0.0015 M sodium citrate (SSC); 0.1% sodium lauryl sulfate (SDS) at 50° C., or (2) employ a denaturing agent such as formamide during hybridization, e.g., 50% formamide with 0.1% bovine serum albumin/0.1% Ficoll/ 0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC and 0.1% SDS. See Sambrook et al., supra, for other examples of stringent conditions.

Uses of Recombinant hK2 Polypeptides and the Preparation of Antibodies Thereto

Once isolated, hK2 polypeptide and its antigenically active variants, derivatives and fragments thereof can be used in assays for hK2 in samples derived from biological materials suspected of containing hK2 or anti-hK2 antibodies, as disclosed in detail in U.S. Pat. No. 5,516,639. For example, the hK2 polypeptide can be labeled with a detectable label, such as via one or more radiolabeled peptidyl residues, and can be used to compete with endogenous hK2 for binding to anti-hK2 antibodies, i.e., as a "capture antigen" to bind to anti-hK2 antibodies in a sample of a physiological fluid, via various competitive immunoassay format for hK2 which uses anti-hK2 antibodies which are capable of immobilization is carried out by:

(a) providing an amount of anti-hK2 antibodies which are capable of attachment to a solid surface;

(b) mixing a physiological sample, which comprises hK2, with a known amount of hK2 polypeptide which comprises a detectable label, to produce a mixed sample;

(c) contacting said antibodies with said mixed sample for a sufficient time to allow immunological reactions to occur between said antibodies and said hK2 to form an antibody-hK2 complex, and between said antibodies and said labeled polypeptide to form an antibody-labeled polypeptide complex;

(d) separating the antibodies which are bound to hK2 and antibodies bound to the labeled polypeptide from the mixed sample;

(e) detecting or determining the presence or amount of labeled polypeptide either bound to the antibodies on the solid surface or remaining in the mixed sample; and (f) determining from the result in step (e) the presence or amount of said hK2 in said sample.

In another format which can detect endogenous hK2 in a sample by a competitive inhibition immunoassay, a known amount of anti-hK2 antibody is added to a sample containing an unknown amount of endogenous hK2. The known amount is selected to be less than the amount required to complex all of the hK2 suspected to be present, e.g., that would be present in a sample of the same amount of sample material obtained from a patient known to be afflicted with breast cancer. Next, a known amount of the hK2 polypeptide of the invention or a subunit thereof, comprising a detectable label is added. If endogenous hK2 is present in the sample, fewer antibodies will be available to bind the labeled hK2 polypeptide, and it will remain free in solution. If no endogenous hK2 is present, the added labeled polypeptide will complex with the added anti-hK2 antibodies to form binary complexes. Next, the binary antibody-antigen complexes are precipitated by an anti-mammal IgG antibody (sheep, goat, mouse, etc.). The amount of radioactivity or other label in the precipitate (a ternary complex) is inversely proportional to the amount of endogenous hK2 that is present in the sample, e.g., a pellet containing reduced amounts of radioactivity is indicative of the presence of endogenous hK2.

Alternatively to the conventional techniques for preparing polyclonal antibodies or antisera in laboratory and farm animals, monoclonal antibodies against hK2 polypeptide can be prepared using known hybridoma cell culture techniques. In general, this method involves prepared an antibody-producing fused cell line, e.g., of primary spleen cells fused with a compatible continuous line of myeloma cells, and growing the fused cells either in mass culture or in an animal species from which the myeloma cell line used was derived or is compatible. Such antibodies offer many advantages in comparison to those produced by inoculation of animals, as they are highly specific and sensitive and relatively "pure" immunochemically. Immunologically active fragments of the present antibodies are also within the scope of the present invention, e.g., the f(ab) fragment, as are chimeric, e.g., partially humanized, monoclonal antibodies.

Chimeric antibodies comprise the fusion of the variable domains from one immunoglobulin to the constant domains from another immunoglobulin. Usually, the variable domains are derived from an immunoglobulin gene from a different species, perhaps a human. This technology is well known to the art. See, for example, European Patent Applications, EP-A-0 125,023 (Cabilly/Genetech) and EP-A-0 120,694 and U.S. Pat. No. 4,816,567, the disclosures of which are incorporated by reference herein, which disclose the preparation of variations of immunoglobulin-type molecules using recombinant DNA technology.

Another approach to prepare chimeric or modified antibodies is to attach the variable region of a monoclonal antibody to another non-immunoglobulin molecule, to produce a derivative chimeric molecule (see WO 86/01533, Neuberger and Rabbits/Celltech, herein incorporated by reference). A further approach is to prepare a chimeric immunoglobulin having different specificities in different variable regions (see EP 68763A). Yet another approach is to introduce a mutation in the DNA encoding the monoclonal antibody, so as to alter certain of its characteristics without changing its essential specificity. This can be accomplished by site-directed mutagenesis or other techniques known in the art.

The Winter patent application EP-A-0 239 400 (herein incorporated by reference) discloses the preparation of an altered, derivative antibody by replacing the complementarity determining regions (CDRs) of a variable region of an immunoglobulin with the CDRs from an immunoglobulin of different specificity, using recombinant DNA techniques ("CDR-grafting"). Thus, CDR-grafting enables "humanization" of antibodies, in combination with the alteration of the framework regions.

Human antibodies can also be prepared by reconstituting the human immune system in mice lacking their native immune system, then immunizing the mice so as to yield human antibodies which are specific for the immunogen.

A "humanized" antibody containing the CDRs of a rodent antibody specific for an antigen of interest may be less likely to be recognized as foreign by the immune system of a human. It follows that a "humanized" antibody with the same binding specificity, as e.g., HK1G464, may be of particular use in human therapy and/or diagnostic methods.

The manipulation and/or alteration of any given antibody, or gene(s) encoding for the same, to generate a derivative antibody is well known to the art.

Detection of hK2-Specific Transcripts by Reverse Transcriptase-Polymerase Chain Reaction RT-PCR)

To detect hK2 encoding RNA transcripts, RNA is isolated from a cellular sample suspected of containing hK2 RNA, e.g., total RNA isolated from human breast tissue. RNA can be isolated by methods known to the art, e.g., using TRI-ZOL™ reagent (GIBCO-BRL/Life Technologies, Gaithersburg, Md.). Oligo-dT, or random-sequence oligonucleotides, as well as sequence-specific oligonucleotides, can be employed as a primer in a reverse transcriptase reaction to prepare first-strand cDNAs from the isolated RNA. See, Sambrook et al., supra. Resultant first-strand cDNAs are then amplified with sequence-specific oligonucleotides in PCR reactions to yield an amplified product.

"Polymerase chain reaction" or "PCR" refers to a procedure or technique in which amounts of a preselected fragment of nucleic acid, RNA and/or DNA, are amplified as described in U.S. Pat. No. 4,683,195. Generally, sequence information from the ends of the region of interest or beyond is employed to design oligonucleotide primers. These primers will be identical or similar in sequence to opposite strands of the template to be amplified. PCR can be used to amplify specific RNA sequences, specific DNA sequences from total genomic DNA, and cDNA transcribed from total cellular RNA, bacteriophage or plasmid sequences, and the like. See generally Mullis et al., *Cold Spring Harbor Symp. Quant. Biol.*, 51, 263 (1987); Erlich, ed., *PCR Technology*, (Stockton Press, NY, 1989). Thus, amplification of specific nucleic acid sequences by PCR relies upon oligonucleotides or "primers" having conserved nucleotide sequences, wherein the conserved sequences are deduced from alignments of related gene or protein sequences, e.g., a sequence comparison of mammalian hK2 genes. For example, one primer is prepared which is predicted to anneal to the antisense strand, and another primer prepared which is predicted to anneal to the sense strand, of a DNA molecule which encodes an hK2 polypeptide.

To detect the amplified product, the reaction mixture is typically subjected to agarose gel electrophoresis or other convenient separation technique, and the presence or absence of the hK2-specific amplified DNA detected. For example, the hK2 amplified DNA may be detected using Southern hybridization with an hK2-specific oligonucleotide probe, or comparing its electrophoretic mobility with DNA standards of known molecular weight. Isolation, purification and characterization of the amplified hK2 DNA may be accomplished by excising or eluting the fragment from the gel (for example, see Lawn et al., *Nucleic Acids Res.*, 2, 6103 (1981), and Goeddel et al., *Nucleic Acids Res.*, 8, 4057 (1980)), cloning the amplified product into a cloning site of a suitable vector, such as the pCRII vector (Invitrogen), sequencing the cloned insert and comparing the DNA sequence to the known sequence of hK2.

The invention will be further described by reference to the following detailed examples.

EXAMPLE 1

Detection of hK2 Expression in a Breast Cancer Cell Line

Materials and Methods

Cell cultures. Several human cell lines (obtained from American Type Culture Collection, Rockville, Md.) including T47-D (breast), ZR75-1 (breast), Hs5787 (breast), BT-20 (breast), MCF-7 (breast), OVCAR-3 (ovary), Hep-G2 (liver), HT-27 (colon), LNCaP (prostate) were propagated in Corning 24-well culture dishes or T175 culture flasks with RPMI 1640 medium supplemented with 5% fetal calf serum at 37° C. and 5% $CO_2$. After reaching approximately 80% confluency, cells were incubated in phenol red-free, serum-free RPMI 1640 medium for 24 hours to deplete undesired steroids.

Steroid treatment. Eleven different steroids were individually added to androgen receptor-positive T47-D cells. Ethanol was used as a solvent to dissolve the steroids. Equivalent amounts of solvent were added to control wells. Steroids were replenished every 24 hours. After a 4-day incubation, spent media was harvested for PSA and hK2 quantitation by an immunometric assay as described below. Cell density was assayed by incubating cells with 150 µl of 3-[4,5-dimethylthiazol-2-yl]-2,5-diphenyl-tetrazolium bromide (MTT) (Sigma, St. Louis, Mo.; 5 mg/ml in PBS) in 1 ml RPMI 1640 per well at 37° C. for 4 hours. The insoluble product of MTT retained in the cells was then dissolved in dimethylsulfoxide (Sigma) for absorbance measurement at 570 nm. The concentrations of PSA and hK2 were normalized by above cell density measurements and expressed as ng/ml/O.D.$_{570}$.

Antibody preparation. Monoclonal antibodies were prepared as described by Grauer et al. (*J. Androl.,* 17, 353–359 (1996)) and Kumar et al. (*Cancer Res.,* 56 5397–5402, 1996)). HK1A523, HK1H449 and HK1H599 are specific for hK2 and HK1H464 is specific for the pro-region of prohK2 (phK2). The pro-region of phK2 contains a 7-amino acid extension at the N-terminus of mature hK2. Recombinant hK2 and prohK2 were expressed and purified using the adenovirus-induced AV12 hamster tumor cell line (Kumar et al., supra). PSA was purified from seminal fluid according to the procedure of Sensabaugh and Blake (*J. Urol,* 144, 1523–1526 (1990)). Hybridoma clones HK1G464.3 and HK1A523 have been deposited with the American Type Culture Collection, in accord with the Budapest Treaty, and granted Accession Nos: HB11983 and HB11876, respectively.

Immunoassays for PSA and hK2 quantitation. PSA levels in culture supernatants were determined by an immunoenzymatic assay using the Tandem-E PSA kit (Hybritech Inc., San Diego, Calif.). Crossreactivity of this assay with hK2 was less than 0.01%.

The levels of hK2 were measured by an immunometric sequential (sandwich) assay with two monoclonal anti-hK2 antibodies, HK1H449 and HK1H599. The crossreactivity of this assay with PSA was less than 0.01%. HK1H449 (the capture antibody) was coated on quarter-inch polystyrene beads (Clifton Plastics) at 1 µg of antibody per bead, and HK1H599 (the detection antibody) was prelabeled with acridinium ester. Recombinant hK2 (2,500 ng/ml) was serially diluted into assay diluent and used as an antigen for the standard curve. The capture antibody on the beads was incubated with the analyte in the sample or standard hK2 solution for 2 hours at 37° C. Any unbound antigen was then washed away. The detecting antibody labeled with acridinium ester was then added to the bead and incubated for 2 hours at 37° C. Washing removed any unreacted excess antibody, leaving the antigen sandwiched between the two mAbs. The chemiluminescent signal (expressed as relative light units or RLU) was then detected in a Magic lite Analyzer II. The unknown sample hK2 concentrations were calculated from the standard curve derived from linear regression of the RLU data.

Northern Blot analysis. Steroid-depleted T47-D cells were cultured in serum free RPMI 1640 with the addition of DHT (100 nM) for 28 hours. Total RNA was extracted by the acidic phenol-chloroform-guanidium thiocyanate method (Young et al., *Biochemistry,* 31, 818–824 (1992)). Equal amounts of RNA (30 µg/lane) were fractionated in the presence of ethidium bromide by denaturing gel electrophoresis and transferred to a Zeta Probe membrane (Bio-Rad, Richmond, Calif.). The amount of RNA used was quantified by spectrophotometric assay at $A_{260}$ in $H_2O$. The Zeta Probe membranes were hybridized with a $^{32}P$-labeled hK2 or PSA probe, prepared as described previously (Young et al., supra) and washed sequentially at 50° C. for 5 minutes with 50 mM $NaH_2PO_4$, pH 7.2, 5% sodium dodecyl sulfate, and 1 mM EDTA, and with 50 mM $NaH_2PO_4$, pH 7.2, 1% sodium dodecyl sulfate, and 1 mM EDTA. The glyceraldehyde-3-phosphate dehydrogenase (GAPDH) complementary DNA labeled with $^{32}P$ by random primer labeling was used for normalization of hK2 mRNA and PSA mRNA. Autoradiographs were obtained by exposing the membrane for 20 hours at −70° C.

Western blot analysis. For direct immunoblotting of hK2 and PSA in spent media from androgen-stimulated T47-D cells, mAb HK1A523 and a polyclonal PSA antibody, specific for hK2 and PSA, respectively, were used as primary antibodies. Serum-free, phenol red-free RPMI-1640 media were harvested from the same number of T47-D cells incubated in the presence or absence of mibolerone for 7 days. Media were concentrated 20-fold by ultrafiltration using Centriplus-3 concentrators (Amicon; Beverly, Mass.). Aliquots of concentrated media were subjected to sodium dodecyl sulfate-polyacrylamide gel electrophoresis (SDS-PAGE) on 12% Tris-Glycine gels. Protein markers (molecular weight range 2530–46000; Amersham, Arlington Heights, Ill.) were run in parallel. Separated proteins were electro-transferred to nitrocellulose membranes (Bio-Rad Laboratories, Hercules, Calif.).

After blocking with 5% non-fat dry milk in TBST buffer (20 mM Tris-HCl/137 mM NaCl/0.1% Tween 20, pH 7.6), the blots were incubated with mAb HK1A523 at 1:5000 dilution or PSA polyclonal antibody at 1:2000 dilution for 1 hour at room temperature. The blots were washed with TBST buffer, and incubated with horseradish peroxidase-conjugated anti-mouse immunoglobulin (Amersham) at 1:10,000 dilution for one hour at room temperature. Following three washes, the blots were incubated for one minute with enhanced chemiluminescence reagents (ECL, Amersham) and exposed to X-film for detection of immunoreactive protein bands. The membrane which was probed with HK1A523 antibody was then stripped and reprobed with phK2-specific HK1H464 antibody.

Reverse Transcriptase-Polymerase Chain Reaction (RT-PCR). Cultured T47-D mibolerone-stimulated cells were harvested and centrifuged at 1000×g, 4° C. for 15 minutes. Total RNA was isolated using acidic phenol-chloroform-guanidium thiocyanate method, as described by Young et al. (*Biochemistry,* 31, 818–824 (1992)). Isolated RNA was then treated with RNase-free DNase1 to remove contaminating genomic DNA.

For RT-PCR, an aliquot (1 µg) of RNA was used for the first strand cDNA synthesis (25 µl final total reaction volume) using either a PSA-specific (5'TCATCTCTGTATCC3'; SEQ ID NO:13) or hK2-specific (5'CATACACCTGTGTC3'; SEQ ID NO:9) primer (100 pmol) and Moloney leukemia virus reverse transcriptase (Gibco BRL, Gaithersburg, Md.). The first strand cDNA was then amplified with a pair of primers (50 pmol each) for PSA, PSA-1 (5'GATGACTCCAGCCACGACCT3'; SEQ ID NO:14) and PSA-2 (5'CACAGACACCCCATCCTATC3'; SEQ ID NO:15) or hK2, hK2-1 (5'GGTGGCTGTGTACAGTCATGGAT3';

SEQ ID NO:10) and hK2-2 (5'CAGAAAGCACAG GTCAGTAGGCA3'; SEQ ID NO:11) using Taq polymerase. Thirty-five to forty cycles of PCR were performed. PCR conditions for each cycle were as follows: denaturation at 94° C. for 60 seconds, annealing at 58° C. (for PSA) or 60° C. (for hK2) for 90 seconds and DNA polymerization at 72° C. for 90 seconds. After PCR cycling, the reactions underwent DNA extension at 72° C. for 10 minutes.

An aliquot of PCR was subjected to electrophoresis on a 1% agarose gel. PCR DNA products in the agarose gel were visualized by ethidium bromide staining. DNA bands corresponding to PSA and hK2 were excised and then eluted from the gel, directly subcloned into pCRII plasmid (Invitrogen, San Diego, Calif.) and transformed into E. coli. Plasmid DNA, containing PSA or hK2 DNA inserts, was prepared, and the inserts sequenced to confirm that the sequence of the inserts corresponded to mRNA of PSA or hK2.

Results

The effect of various steroids on hK2 and PSA production by the breast cancer cell line T47-D are shown in FIG. 1. After 4 days of treatment, androgens, progestins, glucocorticoids and mineralocorticoids induced significant PSA and hK2 expression, while estrogens and an anti-estrogen, tamoxifen, were not stimulatory. The expression of hK2 paralleled that of PSA. Thus, a number of different steroids induce PSA and hK2 in this cell line.

Figure 2:
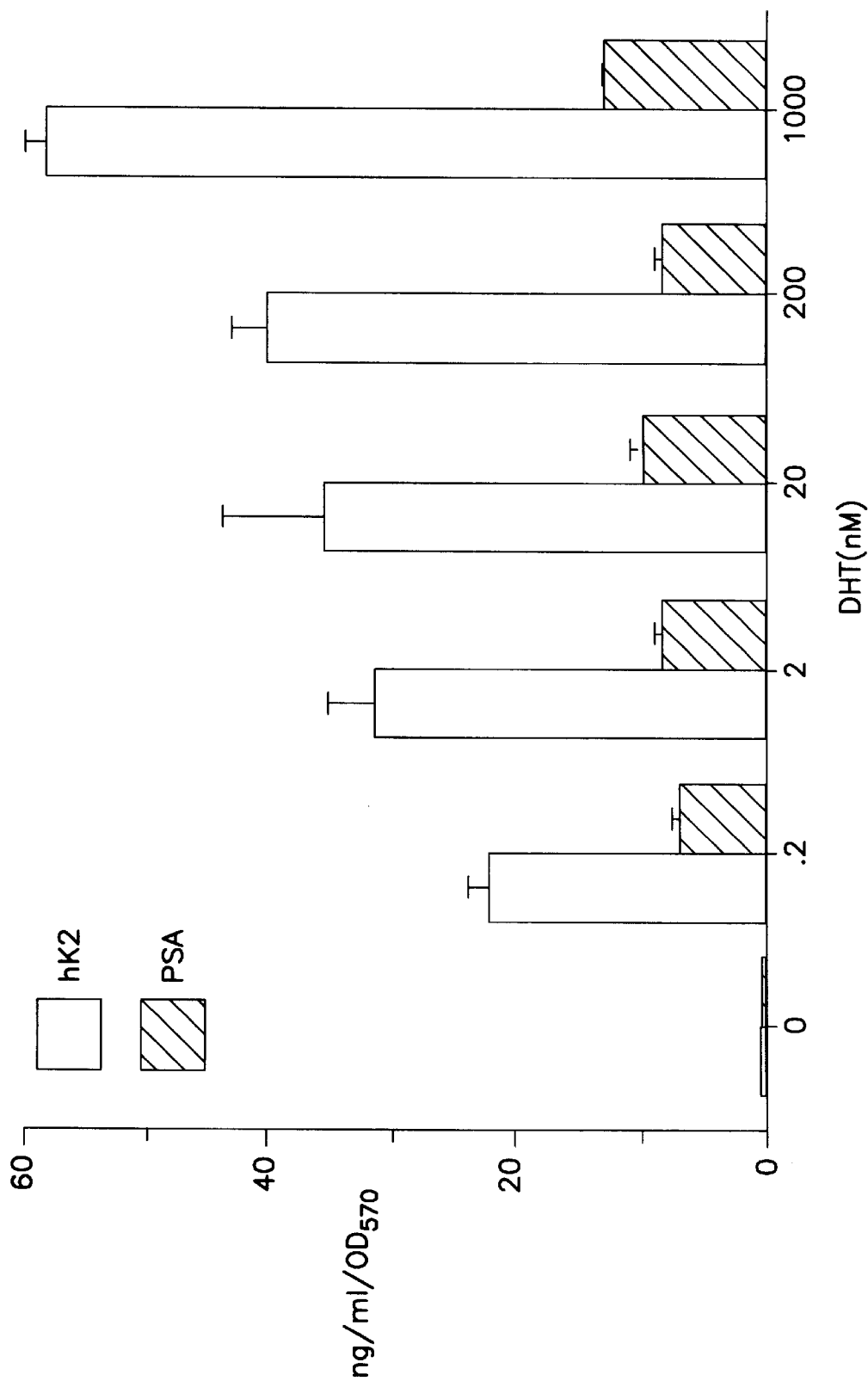
FIG. 2. PSA and hK2 production by T47D cells in response to dihydrotestosterone (DHT). T47-D cells which had been cultured in serum-free media were stimulated with DHT (0.2 nM to 1000 nM). The spent media were collected 4 days post-stimulation.
Figure 3:
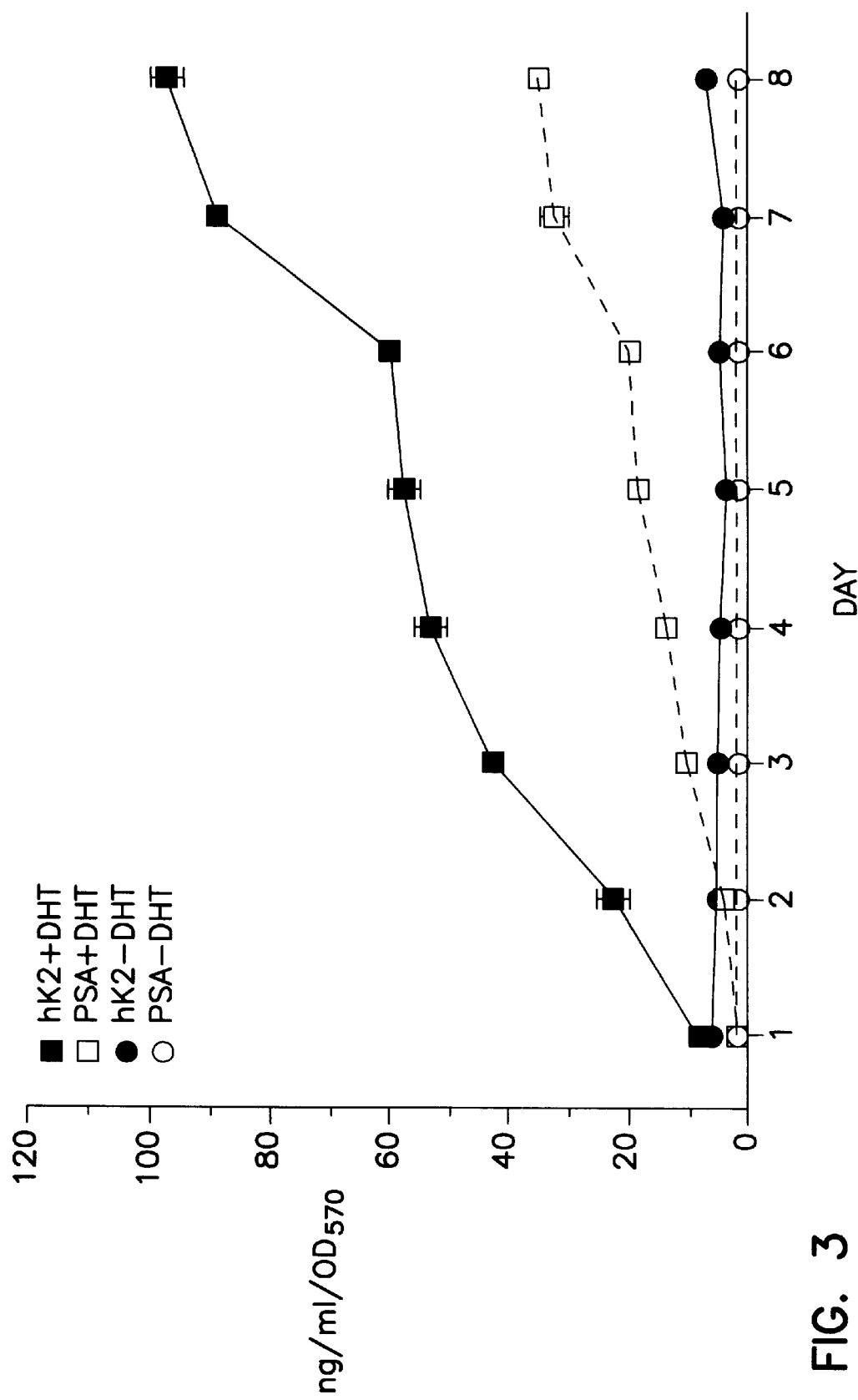
FIG. 3. Accumulation of PSA and hK2 protein from T47-D cells in the presence or absence of DHT stimulation. T47-D cells which had been cultured in serum-free media were grown in the presence or absence of 200 nM DHT for up to 8 days. Steroid was added every 24 hours and spent media were removed for both hK2 and PSA analysis just prior to each stimulation.

To determine whether the effect of the steroids was dose-dependent, T47-D cells were treated with various dihydrotestosterone (DHT) concentrations from 0.2 nM to 1,000 nM. FIG. 2 shows that DHT promoted the induction of hK2 in a dose-dependent manner in T47-D cells. Similarly, the time course effects of 200 nM DHT stimulation on expression of PSA and hK2 were also examined. At 0.2 nM DHT, it appears that PSA induction is maximal. The total amount of PSA polypeptide induced in T47-D cells is 2 to 3-fold lower than that of hK2 polypeptide, which is consistent with the results shown in FIG. 1. Moreover, a time course of DHT stimulation of hK2 and PSA proteins showed that the levels of PSA and hK2 were significantly increased in the media approximately 24 hours after the initial stimulation and increased progressively with time (FIG. 3). Again, more hK2 accumulated in the media with time than did PSA.

Figure 5:
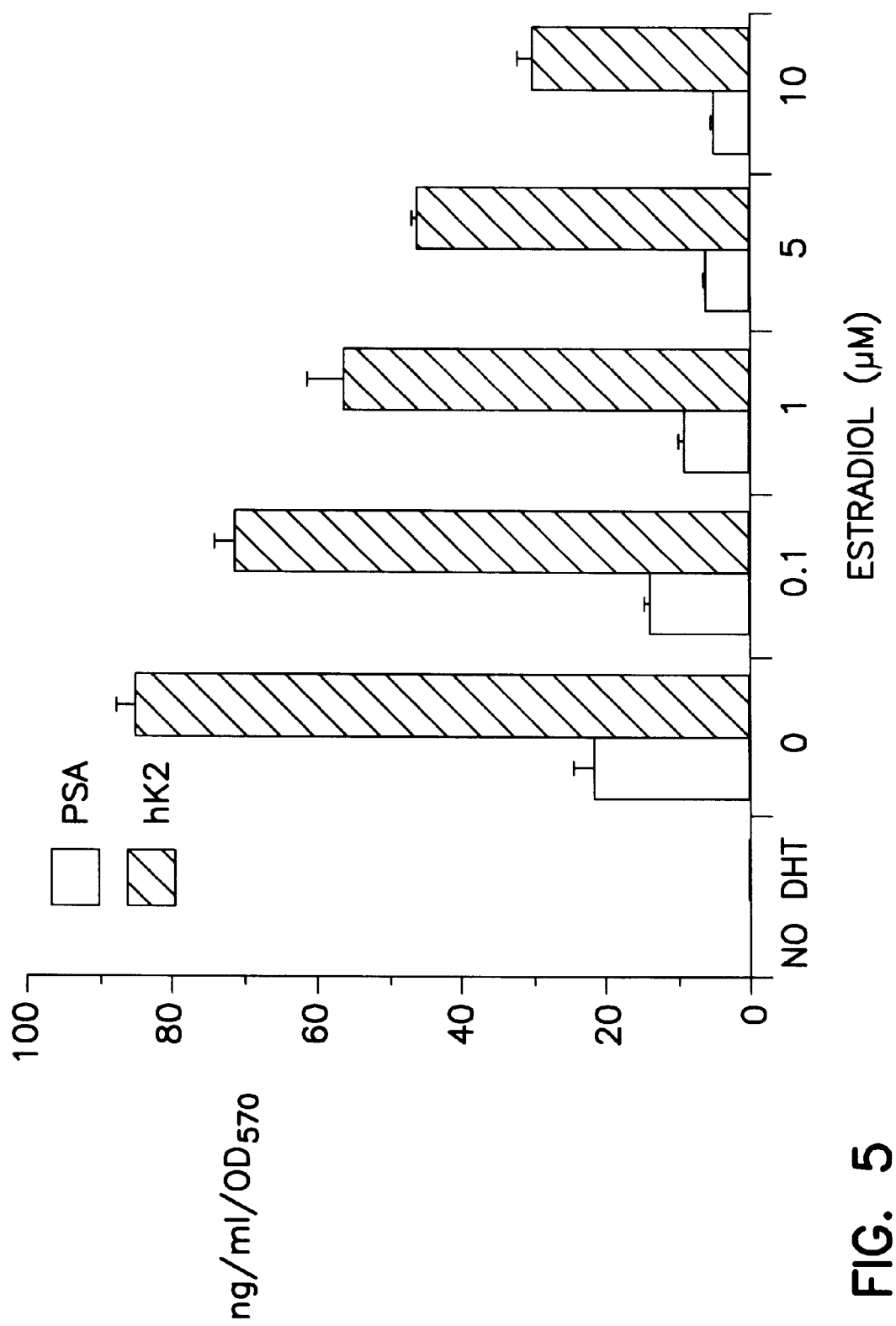
FIG. 5. Inhibition of the stimulatory effect of androgens by estradiol in T47-D cells. T47-D cells which had been cultured in serum-free media were incubated with 50 nM DHT and different concentrations of estradiol. The spent media were harvested 4 days after stimulation.

Experiments were also conducted to test whether hK2 induction by androgens in T47-D cells can be blocked by estrogens. The experiments were performed by stimulating the cells with 50 nM DHT in the presence of different concentrations of estradiol. The results showed that estradiol decreased the stimulatory effect of DHT in a dose-dependent manner (FIG. 5).

Figure 4:
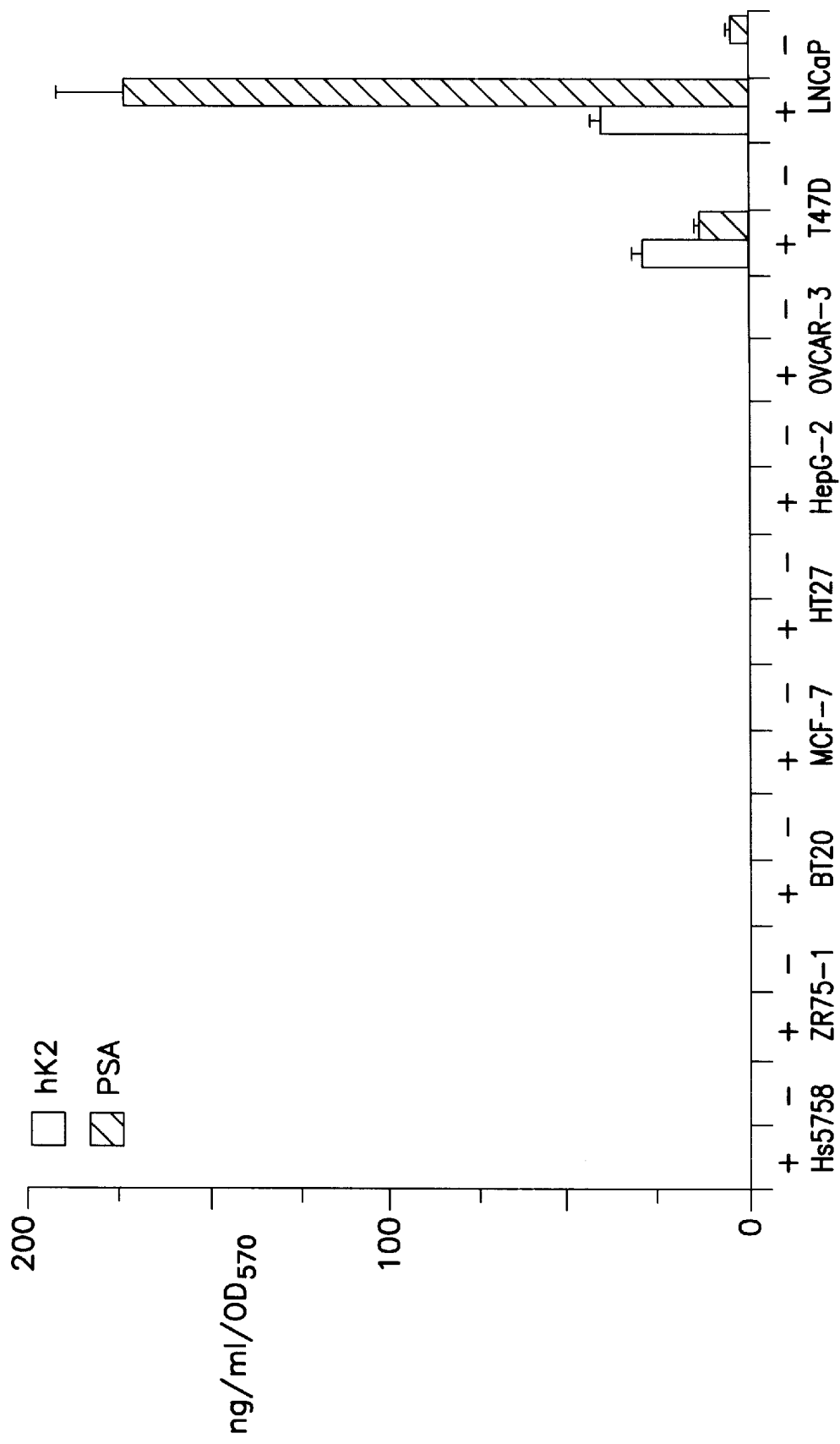
FIG. 4. Production of PSA and hK2 in different human cell lines. Cell lines were propagated in serum-free media and incubated in the presence (+) or absence (−) of a non-metabolizable steroid, mibolerone, for 7 days. The concentration of mibolerone was 3.2 nM for T47-D cells, 1 nM for LNCaP cells, and 10 nM for other cell lines.

Several human cancer cell lines were tested for expression of hK2 and PSA in the presence or absence of androgen stimulation: breast cells (MCF-7, Hs5758, ZR75-1, and BT20), liver cells (Hep-G2), ovarian cells (OVCAR-3), and colon cells (HT27). As shown in FIG. 4, none of these cells produced significant amounts of PSA or hK2 regardless of the presence or absence of androgen. Interestingly, LNCaP cells (an androgen-sensitive prostate cell line) produced higher levels of PSA than hK2. Thus, while the absolute amount of hK2 in the media is similar in LNCaP and T47-D cells, PSA secretion differs widely between the two cell types.

Figure 6C:
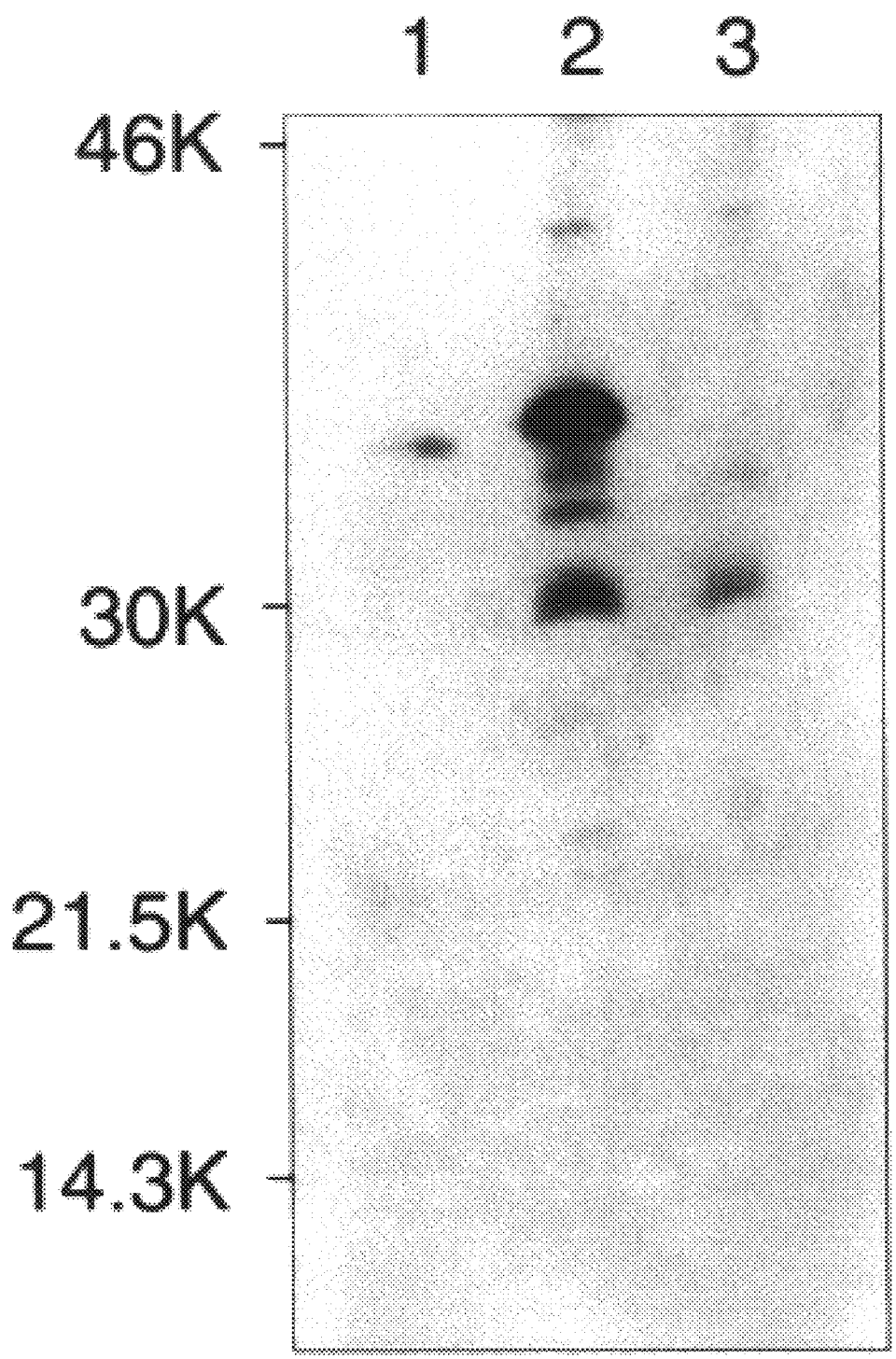
FIG. 6. Western blot analysis of T47-D cell spent media for hK2 and PSA immunoreactivity. Proteins in concentrated spent media were separated by SDS-PAGE (12% polyacrylamide) and blotted onto nitrocellulose. The blots were incubated with anti-hK2 monoclonal antibody (mAb) HK1A523 (A) or rabbit anti-PSA antibody (IgG). (C). The secondary antibody was horseradish peroxidase-labeled anti-mouse IgG, and enhanced chemiluminescence was employed to detect the complexes. The membrane blotted with HK1A523 antibody was then stripped and reprobed with anti-phK2 mAb HK1H464 (B) antibody. A and B lane 1, mature form of recombinant hK2 (50 ng); lane 2, the pro form of recombinant hK2 (50 ng); lane 3, concentrated androgen-induced T47-D cell spent media; lane 4, concentrated control (without androgen stimulation) T47-D cell spent media. (C) lane 1, purified PSA (8 ng); lane 2, concentrated androgen-induced T47-D cell spent media; lane 3, concentrated control T47-D cell spent media.

In order to further characterize the hK2 expression in T47-D cells, a total of 40 ml of spent media from T47-D cells incubated in the presence or absence of 10 nM mibolerone was collected and concentrated to a volume of 2 ml for each sample. An equal volume of each sample was then subjected to SDS-PAGE, run under reducing conditions, and separated proteins were blotted onto a nitrocellulose membrane. Using an hK2-specific antibody, HK1A523, two immunoreactive bands were detected (FIG. 6A). The proteins corresponding to the immunoreactive bands were androgen-inducible.

Unexpectedly, the hK2 protein from T47-D cells seemed to be larger than the mature form of recombinant hK2 which was used as a control (FIG. 6A). One explanation for this observation is that the larger polypeptide is a precursor or zymogen form of hK2: an unprocessed, secretory form of hK2 (e.g., phK2). To test this hypothesis, the monoclonal antibody (mAb) HK1H464, specific for the pro segment of hK2 polypeptide, was used to reprobe the membrane. The prohK2-specific mAb recognized the major protein band, which comigrated with recombinant phK2 protein (FIG. 6A). The minor band was also detected by the antibody, and is likely a degraded or clipped fragment of hK2 retaining the pro-segment epitope. Thus, the results described above suggest that T47-D cells do not produce an hK2-processing protease.

PSA was also detected in androgen-induced spent media of T47-D cells (FIG. 6B). The PSA immunoreactive band was slightly larger than that of purified PSA from seminal fluid.

Figure 7A:
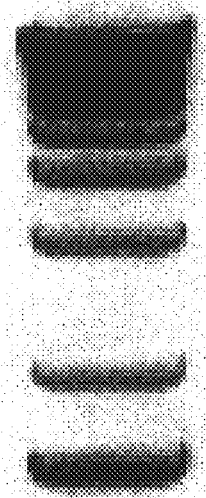
FIG. 7. (A) RT-PCR detection of PSA and hK2 mRNAs in mibolerone-stimulated T47-D cells. MW: 1 Kb DNA Ladder (GibcoBRL, Gaithersburg, Md.). (B) Northern blot analysis of steady-state levels of hK2 and PSA in androgen- or estrogen-stimulated T47-D cells. After 24 hours of steroid depletion, cells were treated as follows: no treatment (0); 100 nM DHT; and 1 μM estradiol ($E_2$). Total RNA was extracted at 28 hours. mRNAs for hK2, PSA and the housekeeping gene, glyceraldehyde-3-phosphate dehydrogenase (GAPDH), in T47-D cells were detected with $^{32}$P-labeled hK2, PSA or GAPDH cDNA probe on the same membrane.
Figure 7A:

To demonstrate that T47-D cells produce hK2 mRNA, total RNA was subjected to RT-PCR utilizing primers specific for either hK2 or PSA RNA transcripts. As seen in FIG. 7A, the results demonstrate hK2 and PSA transcripts are present in androgen-stimulated T47-D cells. The identities of the PCR products were verified by DNA sequencing. Moreover, FIG. 7B shows that the steady-state levels of both hK2 and PSA mRNAs in T47-D cells were not increased by estrogens. Thus, androgens up-regulate the expression of hK2 and PSA in T47-D cells.

Thus, hK2, like PSA, may be involved in growth control in not only prostate but other androgen receptor-positive tissues. Therefore, it is believed that hK2 is a prognostic or predictive marker for breast cancer.

EXAMPLE 2

Detection of hK2 Expression in Breast Tissue

Materials and Methods

Patient Samples. Primary breast tumor tissue is immediately stored in liquid nitrogen after surgical resection and stored subsequently at −70° C. until extraction is performed. For protein analysis, approximately 0.5 g of tumor tissue is weighed out, smashed with a hammer if necessary, and pulverized in a Thermovac tissue pulverizer with liquid $N_2$. The resulting powder is transferred into a 50 mL plastic tube along with 10 mL of extraction buffer (0.01 mol/L Tris, 1.5 mmol/L ethylenediaminetetraacetic acid, 5 mmol/L sodium molybdate, pH adjusted to 7.40 with 5 mol/L HCl). The powder is homogenized on ice with a single 5 second burst of a Polytron homogenizer. The particulate material is pelleted by 1 hour centrifugation at 105,000 g. The intermediate layer (cytosol extract) is collected without disturbing the lipid or particulate layers. Protein concentration of the cytosol extract is determined by the Lowry method and the extracts are stored at −70° C. until analysis.

For RNA analysis, breast tissue RNA is extracted as described in Sambrook et al., supra.

Estrogen and Progesterone Receptors Analyses. Quantitative analysis of estrogen and progesterone receptors (ER, PR) is conducted using the Abbott enzyme immunoassay kits (Abbott Laboratories, North Chicago, Ill. 60064), according to the manufacturer's instructions. However, other methods to measure estrogen and progesterone receptors may be employed, for example, the dextran-coated charcoal method.

p53 and PSA Protein Analyses. Analyses of p53 and PSA are performed by time-resolved fluoroimmunoassay as described in Diamandis (WO 94/27152), which is incorporated by reference herein. PSA levels can also be measured using the Hybritech Tandem-E and -R assays (Hybritech, Inc., San Diego, Calif.), the IMX PSA assay (Abbott Laboratories, Chicago, Ill.), or the DPC IRMA-count PSA assay (Diagnostic Products Corp., Los Angeles, Calif.). For measuring liquid-phase $Tb^{3+}$ fluorescence in white microtiter wells, the CyberFluor 615® Immunoanalyzer, a time-resolved fluorometer, is used. The time-gate settings of the instrument and the interference filter in the emission pathway are the same as described elsewhere (Christopoulous and Diamandis, *Anal. Chem.*, 64, 342–346 (1990); Wang et al., *Cell*, 57, 379–392 (1989)).

hK2 Protein and RNA Analyses. hK2 protein levels in tumor extracts can be determined using methodologies described hereinabove. However, any technique useful to detect hK2 protein may be employed in the practice of the invention including, but not limited to, enzyme immunoassay, radioimmunoassay, chemi- or bioluminescent immunoassay, or fluorescent immunoassay. Thus, for example, a chemiluminescent immunoassay may be employed with acridinium esters as labels, enzymatically triggered chemiluminescence with alkaline phosphatase and dioxetanes substrates, or luminol chemiluminescence enhanced by horseradish peroxidase, an immunoassay using alkaline phosphatase and the fluorogenic substrate 4-methylumbelliferyl phosphate or p-nitrophenyl phosphate, or an immunoassay using horseradish peroxidase and substrates like ABTS and tetramethylbenzidine and time-resolved immunofluorometric assays with $Eu^{3+}$ as label.

High performance liquid chromatography can also be employed to determine hK2 protein levels or amounts. High performance liquid chromatography is performed with a Shimadzu system with an absorbance monitor at 280 nm (Shimadzu Corp., Kyoto, Japan), isocratically, using a mobile phase of 0.1 mol/L $NaH_2SO_4$-0.1 mol/L $NaH_2PO_4$, pH 6.80. Flow rate is 0.5 mL/min. The gel filtration column used is a Bio-Sil SEC-400, 600 mm×7.5 mm (BioRad Labs, Richmond, Calif.). The column is calibrated with a molecular weight standard solution from BioRad, containing thyroglobulin (670 kD), IgG (158 kD) ovalbumin (44 kD), myoglobin (17 kD) and cyanocobalamin (1.4 kD). Fractions of 0.5 mL each are collected with a fraction collector, Model FRAC-100 (Pharmacia, Uppsala, Sweden) after injecting a 150 mL sample. It is anticipated that two peaks may be detected, corresponding to free and antichymotrypsin (ACT)-bound hK2.

The preferred detection method for hK2 RNA is RT-PCR (see Example 1), although other methods for detecting hK2-specific RNA may also be used, such as Northern blot analysis.

Patient Information and Data Analysis. A patient study is conducted to determine the relationship between hK2 expression and ER and/or PR status, breast cancer survival, and response to hormonal therapy, as well as PSA expression and p53 expression. Clinical and pathological information, including clinical stage, histological cell type and grade, axillary node involvement, tumor size, presence of ER and PR in tumor cells and adjuvant treatment after surgery, are collected for each patient. Patients are staged according to the TNM (tumor size, number of affected lymph nodes, and number of metastases) staging system. Each breast cancer specimen is also histologically graded and typed.

Data for hK2, ER and PR, p53 and PSA in tumor extract samples are then analyzed. Tumors are then classified as being positive or negative for ER, PR, p53, and PSA using the following negativity cutoff levels: <10 fmol/mg of total protein for ER and PR (Hassapoglideu et al., *Oncogene* (1993); Thor et al., *J. Natl. Cancer Inst.*, 84, 845–855 (1992); Henderson et al., In: *Breast Diseases*, Harris, Hellman, Henderson and Kinne (eds.), J. P. Lippincott, Philadelphia, pp. 332–346 (1991)); <3 U/L for p53 (equivalent to 0.02 ng/mL); 0.05 µg/L for PSA; and 0.03 µg/L for hK2.

Demographic, clinical and pathological variables, including age, clinical stage, histological grade and type, nodal status, tumor size, ER and PR, and adjuvant treatment, as well as p53 and PSA expression, are compared between hK2-positive and hK2-negative groups, using the contingency table and chi-square test in order to examine the associations between hK2 and these variables. The relationship between each of the study variables and relapse-free or overall survival is expressed by the hazard ratio and its 95% confidence interval, which is calculated univariately using the Cox proportional hazard regression model (Cox, *Stat. Soc.(B)*, 34, 187–202 (1972)). The multivariate Cox regression model is also employed to evaluate the impact of hK2 immunoreactivity on patient survival while controlling for other clinical and pathological variables which may also affect the survival, such as clinical stage (I, II or III/IV), nodal status (positive or negative), tumor size (greater or less than mean size), steroid hormone receptors (presence or absence), and adjuvant treatment (none, tamoxifen, or both tamoxifen and chemotherapy). Kaplan-Meier relapse-free and overall survival curves (Kaplan and Meier, *J. Am. Stat. Assoc.*, 53, 457–481 (1958)) are constructed to demonstrate the survival difference between hK2-positive and negative groups. The log rank test (Mantel, *Cancer Chemoth. Rep.*, 50, 163–170 (1966)) is used to examine the significance of the differences between survival curves.

Patients who possess functional ER and PR are the ones most likely to respond to endocrine treatment which currently consists of administering one or more of the following: antiestrogens, antiprogestins, antiandrogens, progestins, androgens, glucocorticoids. Thus, the correlation of hK2 expression with ER(+) and PR(+) status indicates that the monitoring of hK2 may be a useful test to identify patients who possess functional ER and PR. Therefore, the classification of patients as hK2 (+) and hK2 (−) may be useful to select those who will benefit from endocrine treatment.

In order to examine the prognostic significance of hK2 in the subsets of patients who are ER-negative or ER-positive, the hazard ratio between hK2-positive and hK2-negative patients is calculated for two subsets being the ER-negative and the ER-positive groups, using the Cox regression model. The analysis is done at two cut-off levels of the receptors, 10 fmol/mg or 20 fmol/mg since with the receptor assays used, levels between 10–20 fmol/mg are considered equivocal.

All patents and publications are incorporated by reference herein, as though individually incorporated by reference. Although preferred embodiments of the invention are described herein in detail, it will be understood by those skilled in the art that variations and modifications may be made thereto without departing from the spirit of the invention or the scope of the invention defined by the claims.

What is claimed is:

1. A method for detecting or determining breast cancer in a human, comprising:
   (a) contacting an amount of an antibody, which binds to an hK2 polypeptide and which does not bind to an hK3 polypeptide, with the cells of a human tissue sample so as to form a binary complex comprising the antibody and the cells; and
   (b) determining or detecting the presence or amount of complex formation in the sample and correlating the presence or amount of said complex to the presence or absence of breast cancer in said human.

2. A method for monitoring the progression of breast cancer in a human, comprising:
   (a) contacting an amount of an antibody, which binds to an hK2 polypeptide and which does not bind to an hK3 polypeptide, with the cells of a human tissue sample so as to form a binary complex comprising the antibody and the cells;
   (b) determining or detecting the presence or amount of complex formation in the sample;
   (c) repeating steps (a) and (b) at a point later in time; and
   (d) comparing the result of step (b) with the result of step (c), wherein a difference in the amount of complex formation is indicative of the progression of breast cancer in said human.

3. The method of claim 1 or 2 wherein the antibody is a member of a population of polyclonal antibodies.

4. The method of claim 1 or 2 wherein the antibody is a monoclonal antibody.

5. The method of claim 1 or 2 wherein complex formation is detected by an agent comprising a detectable label or which binds to a detectable label, to form a detectable ternary complex.

6. The method of claim 5 wherein the agent is an antibody.

7. The method of claim 2 wherein the relative amount of one or both of said complexes is compared to a value representative of the amount of one or both of said complexes from a human not at risk of, or afflicted with, breast cancer.

8. The method of claim 1 wherein the relative amount of said complexes is compared to a value representative of the amount of said complexes from a human not at risk of, or afflicted with, breast cancer.

9. The method of claim 1 or 2 wherein the tissue sample is a breast tissue sample.

* * * * *

SEQUENCE LISTING

<160> NUMBER OF SEQ ID NOS: 15

<210> SEQ ID NO 1
<211> LENGTH: 237
<212> TYPE: PRT
<213> ORGANISM: Homo sapiens

<400> SEQUENCE: 1

```
Ile Val Gly Gly Trp Glu Cys Glu Lys His Ser Gln Pro Trp Gln Val
 1               5                  10                  15

Ala Val Tyr Ser His Gly Trp Ala His Cys Gly Gly Val Leu Val His
            20                  25                  30

Pro Gln Trp Val Leu Thr Ala Ala His Cys Leu Lys Lys Asn Ser Gln
        35                  40                  45

Val Trp Leu Gly Arg His Asn Leu Phe Glu Pro Glu Asp Thr Gly Gln
    50                  55                  60

Arg Val Pro Val Ser His Ser Phe Pro His Pro Leu Tyr Asn Met Ser
65                  70                  75                  80

Leu Leu Lys His Gln Ser Leu Arg Pro Asp Glu Asp Ser Ser His Asp
                85                  90                  95

Leu Met Leu Leu Arg Leu Ser Glu Pro Ala Lys Ile Thr Asp Val Val
            100                 105                 110

Lys Val Leu Gly Leu Pro Thr Gln Glu Pro Ala Leu Gly Thr Thr Cys
        115                 120                 125

Tyr Ala Ser Gly Trp Gly Ser Ile Glu Pro Glu Glu Phe Leu Arg Pro
    130                 135                 140

Arg Ser Leu Gln Cys Val Ser Leu His Leu Leu Ser Asn Asp Met Cys
145                 150                 155                 160

Ala Arg Ala Tyr Ser Glu Lys Val Thr Glu Phe Met Leu Cys Ala Gly
                165                 170                 175

Leu Trp Thr Gly Gly Lys Asp Thr Cys Gly Gly Asp Ser Gly Gly Pro
            180                 185                 190

Leu Val Cys Asn Gly Val Leu Gln Gly Ile Thr Ser Trp Gly Pro Glu
        195                 200                 205

Pro Cys Ala Leu Pro Glu Lys Pro Ala Val Tyr Thr Lys Val Val His
    210                 215                 220

Tyr Arg Lys Trp Ile Lys Asp Thr Ile Ala Ala Asn Pro
225                 230                 235
```

<210> SEQ ID NO 2
<211> LENGTH: 711
<212> TYPE: DNA
<213> ORGANISM: Homo sapiens

<400> SEQUENCE: 2

```
attgtgggag gctgggagtg tgagaagcat tcccaaccct ggcaggtggc tgtgtacagt      60
catggatggg cacactgtgg gggtgtcctg gtgcaccccc agtgggtgct cacagctgcc     120
cattgcctaa agaagaatag ccaggtctgg ctgggtcggc acaacctgtt tgagcctgaa     180
gacacaggcc agagggtccc tgtcagccac agcttcccac acccgctcta caatatgagc     240
cttctgaagc atcaaagcct tagaccagat gaagactcca gccatgacct catgctgctc     300
cgcctgtcag agcctgccaa gatcacagat gttgtgaagg tcctgggcct gcccacccag     360
gagccagcac tggggaccac ctgctacgcc tcaggctggg gcagcatcga accagaggag     420
```

```
ttcttgcgcc ccaggagtct tcagtgtgtg agcctccatc tcctgtccaa tgacatgtgt    480
gctagagctt actctgagaa ggtgacagag ttcatgttgt gtgctgggct ctggacaggt    540
ggtaaagaca cttgtggggg tgattctggg ggtccacttg tctgtaatgg tgtgcttcaa    600
ggtatcacat catggggccc tgagccatgt gccctgcctg aaaagcctgc tgtgtacacc    660
aaggtggtgc attaccggaa gtggatcaag gacaccatcg cagccaaccc c            711
```

<210> SEQ ID NO 3
<211> LENGTH: 237
<212> TYPE: PRT
<213> ORGANISM: Homo sapiens

<400> SEQUENCE: 3

```
Ile Val Gly Gly Trp Glu Cys Glu Lys His Ser Gln Pro Trp Gln Val
 1               5                  10                  15

Leu Val Ala Ser Arg Gly Arg Ala Val Cys Gly Gly Val Leu Val His
            20                  25                  30

Pro Gln Trp Val Leu Thr Ala Ala His Cys Ile Arg Asn Lys Ser Val
        35                  40                  45

Ile Leu Leu Gly Arg His Ser Leu Phe His Pro Glu Asp Thr Gly Gln
    50                  55                  60

Val Phe Gln Val Ser His Ser Phe Pro His Pro Leu Tyr Asp Met Ser
65                  70                  75                  80

Leu Leu Lys Asn Arg Phe Leu Arg Pro Gly Asp Asp Ser Ser His Asp
                85                  90                  95

Leu Met Leu Leu Arg Leu Ser Glu Pro Ala Glu Leu Thr Asp Ala Val
            100                 105                 110

Lys Val Met Asp Leu Pro Thr Gln Glu Pro Ala Leu Gly Thr Thr Cys
        115                 120                 125

Tyr Ala Ser Gly Trp Gly Ser Ile Glu Pro Glu Glu Phe Leu Thr Pro
    130                 135                 140

Lys Lys Leu Gln Cys Val Asp Leu His Val Ile Ser Asn Asp Val Cys
145                 150                 155                 160

Ala Gln Val His Pro Gln Lys Val Thr Lys Phe Met Leu Cys Ala Gly
                165                 170                 175

Arg Trp Thr Gly Gly Lys Ser Thr Cys Ser Gly Asp Ser Gly Gly Pro
            180                 185                 190

Leu Val Cys Asn Gly Val Leu Gln Gly Ile Thr Ser Trp Gly Ser Glu
        195                 200                 205

Pro Cys Ala Leu Pro Glu Arg Pro Ser Leu Tyr Thr Lys Val Val His
    210                 215                 220

Tyr Arg Lys Trp Ile Lys Asp Thr Ile Val Ala Asn Pro
225                 230                 235
```

<210> SEQ ID NO 4
<211> LENGTH: 711
<212> TYPE: DNA
<213> ORGANISM: Homo sapiens

<400> SEQUENCE: 4

```
attgtgggag gctgggagtg cgagaagcat tcccaaccct ggcaggtgct tgtggcctct     60
cgtggcaggg cagtctgcgg cggtgttctg gtgcaccccc agtgggtcct cacagctgcc    120
cactgcatca ggaacaaaag cgtgatcttg ctgggtcggc acagcctgtt tcatcctgaa    180
gacacaggcc aggtatttca ggtcagccac agcttcccac accgctcta cgatatgagc    240
```

-continued

```
ctcctgaaga atcgattcct caggccaggt gatgactcca gccacgacct catgctgctc    300
cgcctgtcag agcctgccga gctcacggat gctgtgaagg tcatggacct gcccacccag    360
gagccagcac tggggaccac ctgctacgcc tcaggctggg gcagcattga accagaggag    420
ttcttgaccc caaagaaact tcagtgtgtg gacctccatg ttatttccaa tgacgtgtgt    480
gcgcaagttc accctcagaa ggtgaccaag ttcatgctgt gtgctggacg ctggacaggg    540
ggcaaaagca cctgctcggg tgattctggg ggcccacttg tctgtaatgg tgtgcttcaa    600
ggtatcacgt catggggcag tgaaccatgt gccctgcccg aaaggccttc cctgtacacc    660
aaggtggtgc attaccggaa gtggatcaag gacaccatcg tggccaaccc c             711
```

<210> SEQ ID NO 5
<211> LENGTH: 244
<212> TYPE: PRT
<213> ORGANISM: Homo sapiens

<400> SEQUENCE: 5

```
Val Pro Leu Ile Gln Ser Arg Ile Val Gly Gly Trp Glu Cys Glu Lys
 1               5                  10                  15

His Ser Gln Pro Trp Gln Val Ala Val Tyr Ser His Gly Trp Ala His
             20                  25                  30

Cys Gly Gly Val Leu Val His Pro Gln Trp Val Leu Thr Ala Ala His
         35                  40                  45

Cys Leu Lys Lys Asn Ser Gln Val Trp Leu Gly Arg His Asn Leu Phe
     50                  55                  60

Glu Pro Glu Asp Thr Gly Gln Arg Val Pro Val Ser His Ser Phe Pro
 65                  70                  75                  80

His Pro Leu Tyr Asn Met Ser Leu Leu Lys His Gln Ser Leu Arg Pro
                 85                  90                  95

Asp Glu Asp Ser Ser His Asp Leu Met Leu Leu Arg Leu Ser Glu Pro
            100                 105                 110

Ala Lys Ile Thr Asp Val Val Lys Val Leu Gly Leu Pro Thr Gln Glu
        115                 120                 125

Pro Ala Leu Gly Thr Thr Cys Tyr Ala Ser Gly Trp Gly Ser Ile Glu
    130                 135                 140

Pro Glu Glu Phe Leu Arg Pro Arg Ser Leu Gln Cys Val Ser Leu His
145                 150                 155                 160

Leu Leu Ser Asn Asp Met Cys Ala Arg Ala Tyr Ser Glu Lys Val Thr
                165                 170                 175

Glu Phe Met Leu Cys Ala Gly Leu Trp Thr Gly Gly Lys Asp Thr Cys
            180                 185                 190

Gly Gly Asp Ser Gly Gly Pro Leu Val Cys Asn Gly Val Leu Gln Gly
        195                 200                 205

Ile Thr Ser Trp Gly Pro Glu Pro Cys Ala Leu Pro Glu Lys Pro Ala
    210                 215                 220

Val Tyr Thr Lys Val Val His Tyr Arg Lys Trp Ile Lys Asp Thr Ile
225                 230                 235                 240

Ala Ala Asn Pro
```

<210> SEQ ID NO 6
<211> LENGTH: 766
<212> TYPE: DNA
<213> ORGANISM: Homo sapiens

<400> SEQUENCE: 6

-continued

```
gtgcccctca tccagtctcg gattgtggga ggctgggagt gtgagaagca ttcccaaccc    60
tggcaggtgg ctgtgtacag tcatggatgg cacactgtg ggggtgtcct ggtgcacccc    120
cagtgggtgc tcacagctgc ccattgccta agaagaata gccaggtctg ctgggtcgg    180 cacaacctgt ttgagcctga agacacaggc cagagggtcc ctgtcagcca cagcttccca   240
cacccgctct acaatatgag ccttctgaag catcaaagcc ttagaccaga tgaagactcc   300
agccatgacc tcatgctgct ccgcctgtca gagcctgcca agatcacaga tgttgtgaag   360
gtcctgggcc tgcccaccca ggagccagca ctggggacca cctgctacgc ctcaggctgg   420
ggcagcatcg aaccagagga gttcttgcgc cccaggagtc ttcagtgtgt gagcctccat   480
ctcctgtcca atgacatgtg tgctagagct tactctgaga aggtgacaga gttcatgttg   540
tgtgctgggc tctggacagg tggtaaagac acttgtgggg gtgattctgg gggtccactt   600
gtctgtaatg gtgtgcttca aggtatcaca tcatggggcc ctgagccatg tgccctgcct   660
gaaaagcctg ctgtgtacac caaggtggtg cattaccgga agtggatcaa ggacaccatc   720
gcagccaacc cctgagtgcc cctgtcccac ccctacctct agtaaa              766
```

<210> SEQ ID NO 7
<211> LENGTH: 261
<212> TYPE: PRT
<213> ORGANISM: Homo sapiens

<400> SEQUENCE: 7

```
Met Trp Asp Leu Val Leu Ser Ile Ala Leu Ser Val Gly Cys Thr Gly
  1               5                  10                  15

Ala Val Pro Leu Ile Gln Ser Arg Ile Val Gly Gly Trp Glu Cys Glu
                 20                  25                  30

Lys His Ser Gln Pro Trp Gln Val Ala Val Tyr Ser His Gly Trp Ala
             35                  40                  45

His Cys Gly Gly Val Leu Val His Pro Gln Trp Val Leu Thr Ala Ala
         50                  55                  60

His Cys Leu Lys Lys Asn Ser Gln Val Trp Leu Gly Arg His Asn Leu
 65                  70                  75                  80

Phe Glu Pro Glu Asp Thr Gly Gln Arg Val Pro Val Ser His Ser Phe
                 85                  90                  95

Pro His Pro Leu Tyr Asn Met Ser Leu Leu Lys His Gln Ser Leu Arg
            100                 105                 110

Pro Asp Glu Asp Ser Ser His Asp Leu Met Leu Leu Arg Leu Ser Glu
        115                 120                 125

Pro Ala Lys Ile Thr Asp Val Val Lys Val Leu Gly Leu Pro Thr Gln
    130                 135                 140

Glu Pro Ala Leu Gly Thr Thr Cys Tyr Ala Ser Gly Trp Gly Ser Ile
145                 150                 155                 160

Glu Pro Glu Glu Phe Leu Arg Pro Arg Ser Leu Gln Cys Val Ser Leu
                165                 170                 175

His Leu Leu Ser Asn Asp Met Cys Ala Arg Ala Tyr Ser Glu Lys Val
            180                 185                 190

Thr Glu Phe Met Leu Cys Ala Gly Leu Trp Thr Gly Gly Lys Asp Thr
        195                 200                 205

Cys Gly Gly Asp Ser Gly Gly Pro Leu Val Cys Asn Gly Val Leu Gln
    210                 215                 220

Gly Ile Thr Ser Trp Gly Pro Glu Pro Cys Ala Leu Pro Glu Lys Pro
225                 230                 235                 240
```

```
Ala Val Tyr Thr Lys Val Val His Tyr Arg Lys Trp Ile Lys Asp Thr
            245                 250                 255
Ile Ala Ala Asn Pro
            260

<210> SEQ ID NO 8
<211> LENGTH: 822
<212> TYPE: DNA
<213> ORGANISM: Homo sapiens

<400> SEQUENCE: 8
ggatccagca tgtgggacct ggttctctcc atcgccttgt ctgtggggtg cactggtgcc      60
gtgcccctca tccagtctcg gattgtggga ggctgggagt gtgagaagca ttcccaaccc     120
tggcaggtgg ctgtgtacag tcatggatgg gcacactgtg ggggtgtcct ggtgcacccc     180
cagtgggtgc tcacagctgc ccattgccta agaagaata gccaggtctg ctgggtcgg      240
cacaacctgt ttgagcctga agacacaggc cagagggtcc ctgtcagcca cagcttccca     300
cacccgctct acaatatgag ccttctgaag catcaaagcc ttagaccaga tgaagactcc     360
agccatgacc tcatgctgct ccgcctgtca gagcctgcca agatcacaga tgttgtgaag     420
gtcctgggcc tgcccaccca ggagccagca ctggggacca cctgctacgc ctcaggctgg     480
ggcagcatcg aaccagagga gttcttgcgc cccaggagtc ttcagtgtgt gagcctccat     540
ctcctgtcca atgacatgtg tgctagagct tactctgaga aggtgacaga gttcatgttg     600
tgtgctgggc tctggacagg tggtaaagac acttgtgggg gtgattctgg gggtccactt     660
gtctgtaatg gtgtgcttca aggtatcaca tcatggggcc ctgagccatg tgccctgcct     720
gaaaagcctg ctgtgtacac caaggtggtg cattaccgga gtggatcaa ggacaccatc      780
gcagccaacc cctgagtgcc cctgtcccac ccctacctct ag                        822

<210> SEQ ID NO 9
<211> LENGTH: 14
<212> TYPE: DNA
<213> ORGANISM: Homo sapiens

<400> SEQUENCE: 9
catacacctg tgtc                                                        14

<210> SEQ ID NO 10
<211> LENGTH: 23
<212> TYPE: DNA
<213> ORGANISM: Homo sapiens

<400> SEQUENCE: 10
ggtggctgtg tacagtcatg gat                                              23

<210> SEQ ID NO 11
<211> LENGTH: 23
<212> TYPE: DNA
<213> ORGANISM: Homo sapiens

<400> SEQUENCE: 11
cagaaagcac aggtcagtag gca                                              23

<210> SEQ ID NO 12
<211> LENGTH: 237
<212> TYPE: PRT
<213> ORGANISM: Artificial Sequence
<220> FEATURE:
<223> OTHER INFORMATION: A variant hK2 polypeptide
```

<400> SEQUENCE: 12

```
Ile Val Gly Gly Trp Glu Cys Glu Lys His Ser Gln Pro Trp Gln Val
 1               5                  10                  15
Ala Val Tyr Ser His Gly Trp Ala His Cys Gly Gly Val Leu Val His
             20                  25                  30
Pro Gln Trp Val Leu Thr Ala Ala His Cys Leu Lys Lys Asn Ser Gln
             35                  40                  45
Val Trp Leu Gly Arg His Asn Leu Phe Glu Pro Glu Asp Thr Gly Gln
 50                  55                  60
Arg Val Pro Val Ser His Ser Phe Pro His Pro Leu Tyr Asn Met Ser
 65                  70                  75                  80
Leu Leu Lys His Gln Ser Leu Arg Pro Asp Glu Asp Ser Ser His Asp
                 85                  90                  95
Leu Met Leu Leu Arg Leu Ser Glu Pro Ala Lys Ile Thr Asp Val Val
             100                 105                 110
Lys Val Leu Gly Leu Pro Thr Gln Glu Pro Ala Leu Gly Thr Thr Cys
             115                 120                 125
Tyr Ala Ser Gly Trp Gly Ser Ile Glu Pro Glu Glu Phe Leu Arg Pro
130                 135                 140
Arg Ser Leu Gln Cys Val Ser Leu His Leu Leu Ser Asn Asp Met Cys
145                 150                 155                 160
Ala Arg Ala Tyr Ser Glu Lys Val Thr Glu Phe Met Leu Cys Ala Gly
                165                 170                 175
Leu Trp Thr Gly Gly Lys Asp Thr Cys Gly Asp Ser Gly Gly Pro
             180                 185                 190
Leu Val Cys Asn Gly Val Leu Gln Gly Ile Thr Ser Trp Gly Pro Glu
             195                 200                 205
Pro Cys Ala Leu Pro Glu Lys Pro Val Val Tyr Thr Lys Val Val His
             210                 215                 220
Tyr Arg Lys Trp Ile Lys Asp Thr Ile Ala Ala Asn Pro
225                 230                 235
```

<210> SEQ ID NO 13
<211> LENGTH: 14
<212> TYPE: DNA
<213> ORGANISM: Homo sapiens

<400> SEQUENCE: 13
tcatctctgt atcc    14

<210> SEQ ID NO 14
<211> LENGTH: 20
<212> TYPE: DNA
<213> ORGANISM: Homo sapiens

<400> SEQUENCE: 14
gatgactcca gccacgacct    20

<210> SEQ ID NO 15
<211> LENGTH: 20
<212> TYPE: DNA
<213> ORGANISM: Homo sapiens

<400> SEQUENCE: 15
cacagacacc ccatcctatc    20